(12) United States Patent
Frommer et al.

(10) Patent No.: US 8,357,505 B2
(45) Date of Patent: Jan. 22, 2013

(54) ENVIRONMENTALLY STABLE SENSORS AND METHODS OF USING THE SAME

(75) Inventors: Wolf B. Frommer, Washington, DC (US); Loren Looger, Washington, DC (US)

(73) Assignee: Carnegie Institution of Washington, Washington, DC (US)

( * ) Notice: Subject to any disclaimer, the term of this patent is extended or adjusted under 35 U.S.C. 154(b) by 996 days.

(21) Appl. No.: 11/817,475

(22) PCT Filed: Oct. 14, 2005

(86) PCT No.: PCT/US2005/036954
§ 371 (c)(1),
(2), (4) Date: Jun. 4, 2008

(87) PCT Pub. No.: WO2006/096214
PCT Pub. Date: Sep. 14, 2006

(65) Prior Publication Data
US 2009/0126034 A1    May 14, 2009

Related U.S. Application Data

(60) Provisional application No. 60/658,142, filed on Mar. 4, 2005.

(51) Int. Cl.
*A01K 67/00* (2006.01)
(52) U.S. Cl. ......... 435/29; 435/6.17; 435/243; 536/23.7
(58) Field of Classification Search .................. None
See application file for complete search history.

(56) References Cited

U.S. PATENT DOCUMENTS

| | | | |
|---|---|---|---|
| 5,795,729 A | 8/1998 | Lee | |
| 5,981,200 A | 11/1999 | Tsien | |
| 5,998,204 A | 12/1999 | Tsien | |
| 6,197,534 B1 | 3/2001 | Lakowicz | |
| 6,277,627 B1 | 8/2001 | Hellinga | |
| 6,376,257 B1 | 4/2002 | Persechini | |
| 6,465,199 B1 | 10/2002 | Craig | |
| 6,469,154 B1 | 10/2002 | Tsien | |
| 7,056,683 B2 * | 6/2006 | Ting .............................. | 435/7.1 |
| 2002/0058273 A1 | 5/2002 | Shipwash | |
| 2003/0134346 A1 | 7/2003 | Amiss | |

(Continued)

FOREIGN PATENT DOCUMENTS

| | | | |
|---|---|---|---|
| WO | WO 00/49183 | 8/2000 | |
| WO | 01/18237 | * 3/2001 | |

(Continued)

OTHER PUBLICATIONS

Schaferet al. X-ray structures of the rmltose-maltodextrin-bindingprotein of the thermophilie bacterium *Alicyclobacillus acidocaldarius* provide insight into acid stability of proteins. J. Mol. Biol. Jan. 2, 2004, vol. 335, pp. 261-274.*

(Continued)

*Primary Examiner* — Albert Navarro
*Assistant Examiner* — Ginny Portner
(74) *Attorney, Agent, or Firm* — Morgan, Lewis & Bockius LLP

(57) ABSTRACT

Environmentally stable biosensors are disclosed, which comprise a ligand binding domain from a thermophilic organism conjugated to donor and fluorescent moieties that permit detection and measurement of Fluorescence Resonance Energy Transfer upon ligand binding. Such biosensors demonstrate enhanced acid-, thermal- and chemical stability as compared to sensors constructed using protein domains from mesophilic organisms.

20 Claims, 15 Drawing Sheets

U.S. PATENT DOCUMENTS

| | | | |
|---|---|---|---|
| 2004/0029129 A1 | 2/2004 | Wang | |
| 2004/0118681 A1 | 6/2004 | Hellinga | |
| 2005/0112685 A1 | 5/2005 | Amiss | |
| 2005/0196768 A1 | 9/2005 | Campbell | |
| 2006/0040327 A1* | 2/2006 | Amiss et al. | 435/7.1 |
| 2007/0122881 A1* | 5/2007 | Surber | 435/69.1 |
| 2007/0136825 A1* | 6/2007 | Frommer et al. | 800/3 |
| 2009/0126034 A1* | 5/2009 | Frommer et al. | 800/13 |
| 2009/0188001 A1* | 7/2009 | Frommer et al. | 800/18 |
| 2010/0227374 A1* | 9/2010 | Kim et al. | 435/188 |
| 2011/0111471 A1* | 5/2011 | Kim et al. | 435/137 |
| 2011/0136125 A1* | 6/2011 | Parada Valdecantos et al. | 435/6.12 |

FOREIGN PATENT DOCUMENTS

| | | | |
|---|---|---|---|
| WO | WO 01/18237 | | 3/2001 |
| WO | 03/025220 | * | 3/2003 |
| WO | WO 03/025220 | | 3/2003 |

OTHER PUBLICATIONS

Gardner, MN et al, J. Bacteriology, 2001, vol. 183(11) pp. 3303-3309, Isolation of a New Broad Host Range IncQ-like Plasmid, pTC-F14, from the Acidophilic bacterium *Acidithiobacillus caldus* and Analysis of the Plasmid Replicon.*

Gihring, TM e tal, Extremophiles, 2003, vol. 7, pp. 123-130, Arsenic resistance in the archaeon "*Ferroplasma acidarmanus*": new insights into the structure and evolution of the ars genes.*

Ghauri, MA e tal, Extremophiles, 2003, vol. 7, pp. 341-345, Phylogenetic analysis of different isolates of Sulfobacillus spp. isolated fromuranium-rich environmnets and recovery of gene using integron-specific primers.*

*Thermoplasma acidophophilum*, ATPase subunit EMBL Accession No. AL445063.1, pp. 1-6, Oct. 4, 2000.*

*Thermoplasma aciophilum* maltose binding proteins, pp. 1-3, Accession No. CAC11273.1, year 2000.*

Clark, DA et al, Microbiology, 1996, vol. 142, pp. 785-790, *Acidimicrobium ferrooxidans* gen. nov., sp. nov.:mixed culture ferrous iron oxidation with Sulfobacillus species.*

EMBL Accession No. X62835.1, Nov. 12, 1991, *Alicyclobacillus acidocaldarius*, pp. 1-4, "amy gene for amylase".*

EMBL Accession No. AAL82062., year 2002, *Pyrococcus furiosus*, pp. 1-3, encodes sugar binding protein, malE-like . . . .*

Benson et al. "Design of bioelectronic interfaces by exploiting hinge-bending motions in proteins." Science 293: 1641-1644, 2001.

Blicharska et al. "Fluorescence quenching of Trp Repressor-Operator interaction." Journal of Protein Chemistry 18: 823-830, 1999.

Chen et al. "Protein localization in living cells and tissues using FRET and FLIM." Differentiation 71: 528-541, 2003.

D'Auria et al. "Enzyme fluorescence as a sensing tool: new perspectives in biotechnology." Curr. Opin. in Biotechnol. 12: 99-104, 2001.

De et al. "Novel biosensors for the detection of estrogen receptor ligands." Journal of Steroid Biochemistry and Molecular Biology 96: 235-244, 2005.

De Lorimier et al. "Construction of a fluorescent biosensor family." Protein Science 11: 2655-2575, 2002.

Deuschle et al. "Construction and optimization of a family of genetically encoded metabolite sensors by semirational protein engineering." Protein Science 14: 2304-2314, 2005.

Dwyer et al. "Periplamsic binding proteins: a versatile superfamily for protein engineering." Current Opinion in Structural Biology 14: 495-504, 2004.

Gaits et al. "Shedding light on cell signaling: Interpretation of FRET biosensors." Science's STKE: signal transduction knowledge environment: 165 (PE3): 1-5, 2003.

Gu et al. "A novel analytical method for in vivo phosphate tracking." FEBS Lett. 580: 5885-5893, 2006.

Gunsalus et al. "Nucleotide sequence and expression of *Escherichia coli trpR*, the structural gene for the *trp* aporepressor." PNAS 77: 7117-7121, 1980.

Jenne et al. "Real-time characterization of ribozymes by fluorescence resonance energy transfer (FRET)." Angewandte Chemie 38: 1300-1303, 1999.

Mitra et al. "Fluorescence resonance energy transfer between blue-emitting and red-shifted excitation derivatives of the green fluorescent protein." Gene 173: 13-17, 1996.

Miyawaki et al. "Fluorescent indicators for Ca2+ based on green fluorescent proteins and clamodulin." Nature 388: 882-887, 1997.

Muyan et al. "Fusion estrogen receptor proteins: toward the development of receptor-based agonists and antagonists." Molecular and Cellular Endocrinology 182: 249-263, 2001.

Nagai et al. "A variant of yellow fluorescent protein with fast and efficient maturation for cell-biological application." Nature Biotechnology 20: 87-90, 2002.

Okumoto et al. "Detection of glutamate release from neurons by genetically encoded surface-displayed FRET nanosensors." PNAS 102: 8740-8745, 2005.

Okumoto et al. "Genetically encoded sensors for ions and metabolites." Soil Sci. Plant Nutr. 50: 947-953, 2004.

Salins et al. "Phosphate binding protein as the biorecognition element in a biosensor for phosphate." Sensors and Actuators B 97: 81-89, 2004.

Sigmund "Viewpoint: are studies in genetically altered mice out of control?" Arterioscler. Thromb. Vasc. Biol. 20: 1425-1429, 2000.

Tolosa et al. "Glucose sensor for low-cost lifetime-based sensing using a genetically engineered protein." Analytical Biochemistry 267: 114-120, 1999.

Tsien "Building and breeding molecules to spy on cells and tumors." FEBS Lett. 579: 927-932, 2005.

Widersten et al. "Optimized heterologous expression of the polymorphic human glutathione transferase M1-1 based on silent mutations in the corresponding cDNA." Protein Expression and Purification 7: 367-371, 1996.

Wood et al. PRI-80 Database, Accession No. AI2966, Jul. 9, 2004, The Genome of the Natural Genetic Engineer *Agrobacterium tumefaciens* C58, Yoo et al. Science 294: 2317-2323, 2001.

Xu et al. "Kinetic and thermodynamic studies of purine repressor binding to corepressor and operator DNA." Journal of Biological Chemistry 273: 8058-8064, 1998.

Zhang et al. "Genetically encoded reporters of protein kinase A activity reveal impact of substrate tethering." PNAS 98: 14997-15002, 2001.

Fehr et al. (2002) Visualization of maltose uptake in living yeast cells by fluorescent nanosensors, PNAS, 99(15):9846-9851.

Schafer et al. (2004) X-ray structures of maltose-maltodextrin-binding protein of the thermoacidophilic bacterium *Alicyclobacillus acidocaldarius* provide insight into acid stability of proteins, J. Mol. Biol., 335:261-274.

* cited by examiner

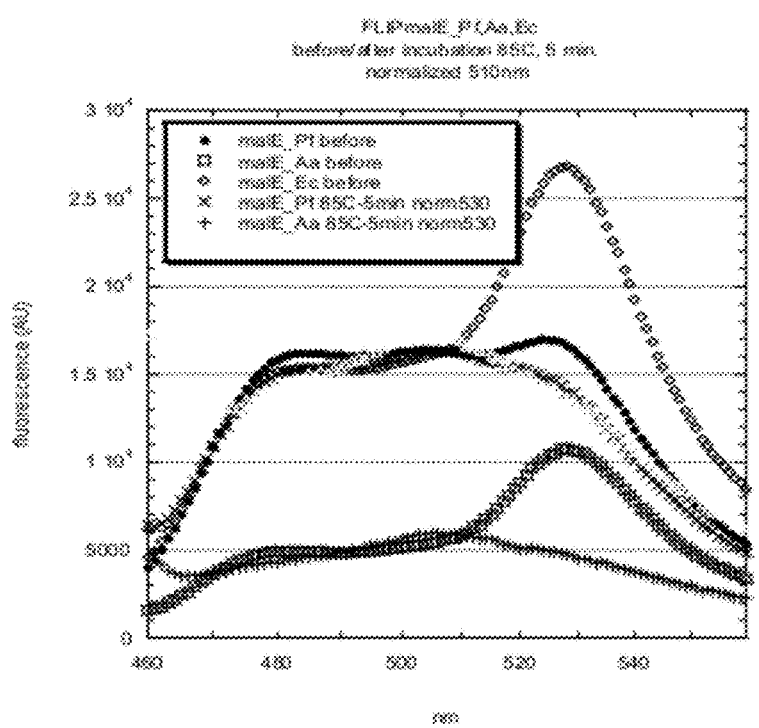

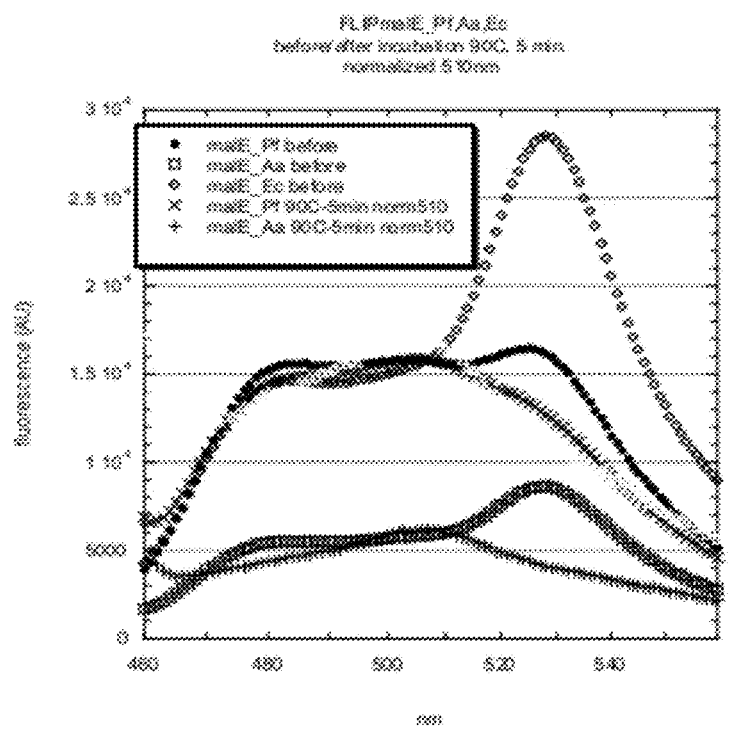
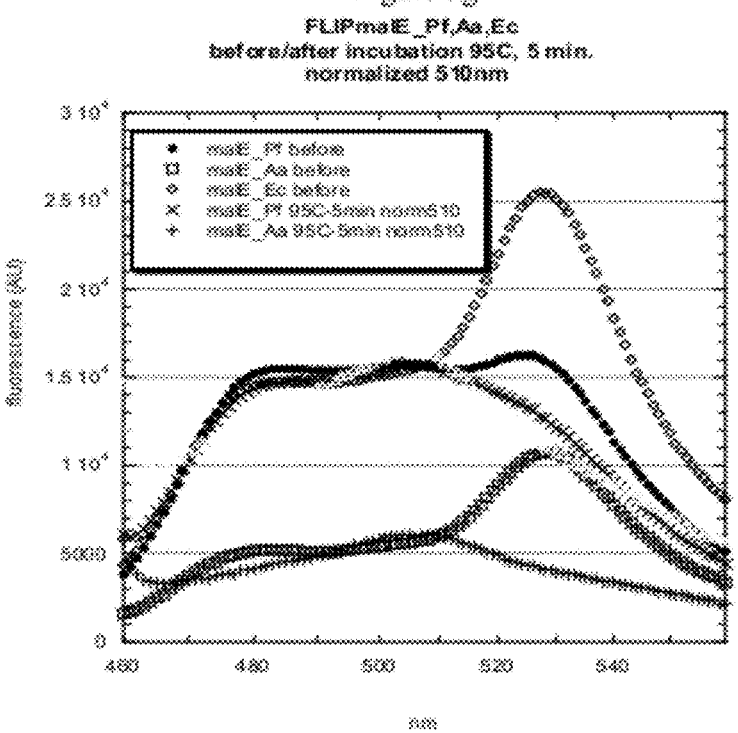

SEQUENCE LISTING

```
<160> NUMBER OF SEQ ID NOS: 4

<210> SEQ ID NO 1
<211> LENGTH: 2694
<212> TYPE: DNA
<213> ORGANISM: Pyrococcus furiosus
<220> FEATURE:
<221> NAME/KEY: CDS
<222> LOCATION: (1)..(2694)

<400> SEQUENCE: 1 atg cgg ggt tct cat cat cat cat cat cat ggt atg gct agc atg act      48
Met Arg Gly Ser His His His His His His Gly Met Ala Ser Met Thr
1               5                   10                  15 ggt gga cag caa atg ggt cgg gat ctg tac gac gat gac gat aag gat      96
```

```
                                                    -continued

Gly Gly Gln Gln Met Gly Arg Asp Leu Tyr Asp Asp Asp Lys Asp
            20                  25                  30 ccg ggc cgc atg gtg agc aag ggc gag gag ctg ttc acc ggg gtg gtg        144
Pro Gly Arg Met Val Ser Lys Gly Glu Glu Leu Phe Thr Gly Val Val
            35                  40                  45 ccc atc ctg gtc gag ctg gac ggc gac gta aac ggc cac aag ttc agc        192
Pro Ile Leu Val Glu Leu Asp Gly Asp Val Asn Gly His Lys Phe Ser
 50                  55                  60 gtg tcc ggc gag ggc gag ggc gat gcc acc tac ggc aag ctg acc ctg        240
Val Ser Gly Glu Gly Glu Gly Asp Ala Thr Tyr Gly Lys Leu Thr Leu
 65                  70                  75                  80 aag ttc atc tgc acc acc ggc aag ctg ccc gtg ccc tgg ccc acc ctc        288
Lys Phe Ile Cys Thr Thr Gly Lys Leu Pro Val Pro Trp Pro Thr Leu
            85                  90                  95 gtg acc acc ctg acc tgg ggc gtg cag tgc ttc agc cgc tac ccc gac        336
Val Thr Thr Leu Thr Trp Gly Val Gln Cys Phe Ser Arg Tyr Pro Asp
            100                 105                 110 cac atg aag cag cac gac ttc ttc aag tcc gcc atg ccc gaa ggc tac        384
His Met Lys Gln His Asp Phe Phe Lys Ser Ala Met Pro Glu Gly Tyr
            115                 120                 125 gtc cag gag cgc acc atc ttc ttc aag gac gac ggc aac tac aag acc        432
Val Gln Glu Arg Thr Ile Phe Phe Lys Asp Asp Gly Asn Tyr Lys Thr
            130                 135                 140 cgc gcc gag gtg aag ttc gag ggc gac acc ctg gtg aac cgc atc gag        480
Arg Ala Glu Val Lys Phe Glu Gly Asp Thr Leu Val Asn Arg Ile Glu
145                 150                 155                 160 ctg aag ggc atc gac ttc aag gag gac ggc aac atc ctg ggg cac aag        528
Leu Lys Gly Ile Asp Phe Lys Glu Asp Gly Asn Ile Leu Gly His Lys
            165                 170                 175 ctg gag tac aac tac atc agc cac aac gtc tat atc acc gcc gac aag        576
Leu Glu Tyr Asn Tyr Ile Ser His Asn Val Tyr Ile Thr Ala Asp Lys
            180                 185                 190 cag aag aac ggc atc aag gcc aac ttc aag atc cgc cac aac atc gag        624
Gln Lys Asn Gly Ile Lys Ala Asn Phe Lys Ile Arg His Asn Ile Glu
            195                 200                 205 gac ggc agc gtg cag ctc gcc gac cac tac cag cag aac acc ccc atc        672
Asp Gly Ser Val Gln Leu Ala Asp His Tyr Gln Gln Asn Thr Pro Ile
210                 215                 220 ggc gac ggc ccc gtg ctg ctg ccc gac aac cac tac ctg agc acc cag        720
Gly Asp Gly Pro Val Leu Leu Pro Asp Asn His Tyr Leu Ser Thr Gln
225                 230                 235                 240 tcc gcc ctg agc aaa gac ccc aac gag aag cgc gat cac atg gtc ctg        768
Ser Ala Leu Ser Lys Asp Pro Asn Glu Lys Arg Asp His Met Val Leu
            245                 250                 255 ctg gag ttc gtg acc gcc gcc ggg atc act ctc ggc atg gac gag ctg        816
Leu Glu Phe Val Thr Ala Ala Gly Ile Thr Leu Gly Met Asp Glu Leu
            260                 265                 270 tac aag ggt ggt acc gga ggc gcc aaa gtt gtt att tgg cat gca atg        864
Tyr Lys Gly Gly Thr Gly Gly Ala Lys Val Val Ile Trp His Ala Met
            275                 280                 285 caa ccc aat gag ctt gag gtc ttc caa agc tta gcg gaa gaa tac atg        912
Gln Pro Asn Glu Leu Glu Val Phe Gln Ser Leu Ala Glu Glu Tyr Met
            290                 295                 300 gca ctc tgt cca gaa gtt gag ata gtt ttt gaa caa aag cca aac ttg        960
Ala Leu Cys Pro Glu Val Glu Ile Val Phe Glu Gln Lys Pro Asn Leu
305                 310                 315                 320 gaa gat gct ctt aag gct gca ata ccc aca ggt caa ggt cct gac ctc       1008
Glu Asp Ala Leu Lys Ala Ala Ile Pro Thr Gly Gln Gly Pro Asp Leu
            325                 330                 335 ttt atc tgg gct cac gac tgg att gga aag ttt gct gag gca gga tta       1056
```

-continued

| | | | | | | | | | | | | | | |
|---|---|---|---|---|---|---|---|---|---|---|---|---|---|---|
| Phe | Ile | Trp | Ala | His | Asp | Trp | Ile | Gly | Lys | Phe | Ala | Glu | Ala | Gly | Leu |
| | | | 340 | | | | 345 | | | | 350 | | | | |

| ctt | gag | cca | att | gat | gaa | tat | gta | act | gaa | gat | ctc | ctt | aac | gag | ttt | 1104 |
|---|---|---|---|---|---|---|---|---|---|---|---|---|---|---|---|---|
| Leu | Glu | Pro | Ile | Asp | Glu | Tyr | Val | Thr | Glu | Asp | Leu | Leu | Asn | Glu | Phe | |
| | 355 | | | | 360 | | | | 365 | | | | | | | |

| gct | cca | atg | gcc | cag | gat | gca | atg | cag | tat | aaa | ggt | cac | tac | tat | gct | 1152 |
|---|---|---|---|---|---|---|---|---|---|---|---|---|---|---|---|---|
| Ala | Pro | Met | Ala | Gln | Asp | Ala | Met | Gln | Tyr | Lys | Gly | His | Tyr | Tyr | Ala | |
| 370 | | | | 375 | | | | | 380 | | | | | | | |

| cta | cca | ttc | gcc | gct | gaa | aca | gtt | gca | ata | atc | tac | agc | aaa | gaa | atg | 1200 |
|---|---|---|---|---|---|---|---|---|---|---|---|---|---|---|---|---|
| Leu | Pro | Phe | Ala | Ala | Glu | Thr | Val | Ala | Ile | Ile | Tyr | Ser | Lys | Glu | Met | |
| 385 | | | | 390 | | | | | 395 | | | | | 400 | | |

| gtt | agc | gag | cca | ccg | aaa | acc | ttt | gat | gag | atg | aag | gca | ata | atg | gag | 1248 |
|---|---|---|---|---|---|---|---|---|---|---|---|---|---|---|---|---|
| Val | Ser | Glu | Pro | Pro | Lys | Thr | Phe | Asp | Glu | Met | Lys | Ala | Ile | Met | Glu | |
| | | | | 405 | | | | 410 | | | | | 415 | | | |

| aag | tac | tat | gat | cca | gca | aat | gag | aag | tat | gga | ata | gct | tgg | cca | att | 1296 |
|---|---|---|---|---|---|---|---|---|---|---|---|---|---|---|---|---|
| Lys | Tyr | Tyr | Asp | Pro | Ala | Asn | Glu | Lys | Tyr | Gly | Ile | Ala | Trp | Pro | Ile | |
| | | | 420 | | | | | 425 | | | | | 430 | | | |

| aat | gcc | tac | ttt | atc | tca | gca | att | gct | cag | gcc | ttt | ggt | ggt | tac | tac | 1344 |
|---|---|---|---|---|---|---|---|---|---|---|---|---|---|---|---|---|
| Asn | Ala | Tyr | Phe | Ile | Ser | Ala | Ile | Ala | Gln | Ala | Phe | Gly | Gly | Tyr | Tyr | |
| | | | 435 | | | | | 440 | | | | | 445 | | | |

| ttt | gac | gac | aaa | aca | gag | caa | ccg | gga | cta | gat | aag | cct | gag | aca | atc | 1392 |
|---|---|---|---|---|---|---|---|---|---|---|---|---|---|---|---|---|
| Phe | Asp | Asp | Lys | Thr | Glu | Gln | Pro | Gly | Leu | Asp | Lys | Pro | Glu | Thr | Ile | |
| 450 | | | | | 455 | | | | | 460 | | | | | | |

| gaa | gga | ttt | aag | ttc | ttc | ttc | aca | gaa | ata | tgg | cca | tac | atg | gct | cca | 1440 |
|---|---|---|---|---|---|---|---|---|---|---|---|---|---|---|---|---|
| Glu | Gly | Phe | Lys | Phe | Phe | Phe | Thr | Glu | Ile | Trp | Pro | Tyr | Met | Ala | Pro | |
| 465 | | | | | 470 | | | | | 475 | | | | | 480 | |

| act | gga | gac | tac | aac | act | caa | cag | agt | ata | ttc | ctc | gag | ggt | aga | gcc | 1488 |
|---|---|---|---|---|---|---|---|---|---|---|---|---|---|---|---|---|
| Thr | Gly | Asp | Tyr | Asn | Thr | Gln | Gln | Ser | Ile | Phe | Leu | Glu | Gly | Arg | Ala | |
| | | | | 485 | | | | | 490 | | | | | 495 | | |

| cca | atg | atg | gtt | aat | ggt | cca | tgg | agc | att | aac | gac | gtt | aag | aag | gca | 1536 |
|---|---|---|---|---|---|---|---|---|---|---|---|---|---|---|---|---|
| Pro | Met | Met | Val | Asn | Gly | Pro | Trp | Ser | Ile | Asn | Asp | Val | Lys | Lys | Ala | |
| | | | 500 | | | | | 505 | | | | | 510 | | | |

| gga | ata | aac | ttt | gga | gtg | gtt | cca | cta | cct | cca | ata | atc | aag | gat | ggt | 1584 |
|---|---|---|---|---|---|---|---|---|---|---|---|---|---|---|---|---|
| Gly | Ile | Asn | Phe | Gly | Val | Val | Pro | Leu | Pro | Pro | Ile | Ile | Lys | Asp | Gly | |
| | | | 515 | | | | | 520 | | | | | 525 | | | |

| aag | gag | tac | tgg | cca | agg | cct | tac | ggt | gga | gtt | aag | ttg | att | tac | ttc | 1632 |
|---|---|---|---|---|---|---|---|---|---|---|---|---|---|---|---|---|
| Lys | Glu | Tyr | Trp | Pro | Arg | Pro | Tyr | Gly | Gly | Val | Lys | Leu | Ile | Tyr | Phe | |
| | 530 | | | | | 535 | | | | | 540 | | | | | |

| gca | gcg | gga | ata | aag | aac | aag | gat | gct | gca | tgg | aag | ttc | gca | aag | tgg | 1680 |
|---|---|---|---|---|---|---|---|---|---|---|---|---|---|---|---|---|
| Ala | Ala | Gly | Ile | Lys | Asn | Lys | Asp | Ala | Ala | Trp | Lys | Phe | Ala | Lys | Trp | |
| 545 | | | | | 550 | | | | | 555 | | | | | 560 | |

| ctt | acc | acg | agc | gaa | gag | tca | att | aag | aca | ttg | gca | cta | gag | ctg | gga | 1728 |
|---|---|---|---|---|---|---|---|---|---|---|---|---|---|---|---|---|
| Leu | Thr | Thr | Ser | Glu | Glu | Ser | Ile | Lys | Thr | Leu | Ala | Leu | Glu | Leu | Gly | |
| | | | | 565 | | | | | 570 | | | | | 575 | | |

| tac | ata | ccg | gtt | ctt | acg | aag | gtt | ctt | gat | gat | cca | gaa | att | aag | aat | 1776 |
|---|---|---|---|---|---|---|---|---|---|---|---|---|---|---|---|---|
| Tyr | Ile | Pro | Val | Leu | Thr | Lys | Val | Leu | Asp | Asp | Pro | Glu | Ile | Lys | Asn | |
| | | | 580 | | | | | 585 | | | | | 590 | | | |

| gat | cca | gta | atc | tat | ggc | ttt | gga | caa | gca | gtt | cag | cac | gca | tac | cta | 1824 |
|---|---|---|---|---|---|---|---|---|---|---|---|---|---|---|---|---|
| Asp | Pro | Val | Ile | Tyr | Gly | Phe | Gly | Gln | Ala | Val | Gln | His | Ala | Tyr | Leu | |
| | | | 595 | | | | | 600 | | | | | 605 | | | |

| atg | cca | aag | agt | cca | aag | atg | agt | gct | gtt | tgg | ggc | gga | gtt | gat | ggg | 1872 |
|---|---|---|---|---|---|---|---|---|---|---|---|---|---|---|---|---|
| Met | Pro | Lys | Ser | Pro | Lys | Met | Ser | Ala | Val | Trp | Gly | Gly | Val | Asp | Gly | |
| 610 | | | | | 615 | | | | | 620 | | | | | | |

| gca | att | aac | gaa | atc | ctc | caa | gat | cca | caa | aac | gct | gac | att | gaa | gga | 1920 |
|---|---|---|---|---|---|---|---|---|---|---|---|---|---|---|---|---|
| Ala | Ile | Asn | Glu | Ile | Leu | Gln | Asp | Pro | Gln | Asn | Ala | Asp | Ile | Glu | Gly | |
| 625 | | | | | 630 | | | | | 635 | | | | | 640 | |

| ata | cta | aag | aag | tat | caa | caa | gaa | atc | ctt | aac | aac | atg | caa | ggt | acc | 1968 |
|---|---|---|---|---|---|---|---|---|---|---|---|---|---|---|---|---|
| Ile | Leu | Lys | Lys | Tyr | Gln | Gln | Glu | Ile | Leu | Asn | Asn | Met | Gln | Gly | Thr | |
| | | | | 645 | | | | | 650 | | | | | 655 | | |

| ggt | gga | atg | gtg | agc | aag | ggc | gag | gag | ctg | ttc | acc | ggg | gtg | gtg | ccc | 2016 |

-continued

```
                Gly Gly Met Val Ser Lys Gly Glu Glu Leu Phe Thr Gly Val Val Pro
                            660                 665                 670 atc ctg gtc gag ctg gac ggc gac gta aac ggc cac aag ttc agc gtg       2064
Ile Leu Val Glu Leu Asp Gly Asp Val Asn Gly His Lys Phe Ser Val
            675                 680                 685 tcc ggc gag ggc gag ggc gat gcc acc tac ggc aag ctg acc ctg aag       2112
Ser Gly Glu Gly Glu Gly Asp Ala Thr Tyr Gly Lys Leu Thr Leu Lys
        690                 695                 700 ttc atc tgc acc acc ggc aag ctg ccc gtg ccc tgg ccc acc ctc gtg       2160
Phe Ile Cys Thr Thr Gly Lys Leu Pro Val Pro Trp Pro Thr Leu Val
705                 710                 715                 720 acc acc ttc ggc tac ggc ctg cag tgc ttc gcc cgc tac ccc gac cac       2208
Thr Thr Phe Gly Tyr Gly Leu Gln Cys Phe Ala Arg Tyr Pro Asp His
                725                 730                 735 atg aag cag cac gac ttc ttc aag tcc gcc atg ccc gaa ggc tac gtc       2256
Met Lys Gln His Asp Phe Phe Lys Ser Ala Met Pro Glu Gly Tyr Val
            740                 745                 750 cag gag cgc acc atc ttc ttc aag gac gac ggc aac tac aag acc cgc       2304
Gln Glu Arg Thr Ile Phe Phe Lys Asp Asp Gly Asn Tyr Lys Thr Arg
        755                 760                 765 gcc gag gtg aag ttc gag ggc gac acc ctg gtg aac cgc atc gag ctg       2352
Ala Glu Val Lys Phe Glu Gly Asp Thr Leu Val Asn Arg Ile Glu Leu
    770                 775                 780 aag ggc atc gac ttc aag gag gac ggc aac atc ctg ggg cac aag ctg       2400
Lys Gly Ile Asp Phe Lys Glu Asp Gly Asn Ile Leu Gly His Lys Leu
785                 790                 795                 800 gag tac aac tac aac agc cac aac gtc tat atc atg gcc gac aag cag       2448
Glu Tyr Asn Tyr Asn Ser His Asn Val Tyr Ile Met Ala Asp Lys Gln
                805                 810                 815 aag aac ggc atc aag gtg aac ttc aag atc cgc cac aac atc gag gac       2496
Lys Asn Gly Ile Lys Val Asn Phe Lys Ile Arg His Asn Ile Glu Asp
            820                 825                 830 ggc agc gtg cag ctc gcc gac cac tac cag cag aac acc ccc atc ggc       2544
Gly Ser Val Gln Leu Ala Asp His Tyr Gln Gln Asn Thr Pro Ile Gly
        835                 840                 845 gac ggc ccc gtg ctg ctg ccc gac aac cac tac ctg agc tac cag tcc       2592
Asp Gly Pro Val Leu Leu Pro Asp Asn His Tyr Leu Ser Tyr Gln Ser
    850                 855                 860 gcc ctg agc aaa gac ccc aac gag aag cgc gat cac atg gtc ctg ctg       2640
Ala Leu Ser Lys Asp Pro Asn Glu Lys Arg Asp His Met Val Leu Leu
865                 870                 875                 880 gag ttc gtg acc gcc gcc ggg atc act ctc ggc atg gac gag ctg tac       2688
Glu Phe Val Thr Ala Ala Gly Ile Thr Leu Gly Met Asp Glu Leu Tyr
                885                 890                 895 aag taa                                                                2694
Lys

<210> SEQ ID NO 2
<211> LENGTH: 897
<212> TYPE: PRT
<213> ORGANISM: Pyrococcus furiosus

<400> SEQUENCE: 2

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Gly Arg Met Val Ser Lys Gly Glu Glu Leu Phe Thr Gly Val Val
        35                  40                  45

Pro Ile Leu Val Glu Leu Asp Gly Asp Val Asn Gly His Lys Phe Ser
```

-continued

```
            50                  55                  60
Val Ser Gly Glu Gly Glu Gly Asp Ala Thr Tyr Gly Lys Leu Thr Leu
65                  70                  75                  80

Lys Phe Ile Cys Thr Thr Gly Lys Leu Pro Val Pro Trp Pro Thr Leu
                85                  90                  95

Val Thr Thr Leu Thr Trp Gly Val Gln Cys Phe Ser Arg Tyr Pro Asp
                100                 105                 110

His Met Lys Gln His Asp Phe Phe Lys Ser Ala Met Pro Glu Gly Tyr
                115                 120                 125

Val Gln Glu Arg Thr Ile Phe Phe Lys Asp Asp Gly Asn Tyr Lys Thr
130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Ile Ser His Asn Val Tyr Ile Thr Ala Asp Lys
                180                 185                 190

Gln Lys Asn Gly Ile Lys Ala Asn Phe Lys Ile Arg His Asn Ile Glu
                195                 200                 205

Asp Gly Ser Val Gln Leu Ala Asp His Tyr Gln Gln Asn Thr Pro Ile
210                 215                 220

Gly Asp Gly Pro Val Leu Leu Pro Asp Asn His Tyr Leu Ser Thr Gln
225                 230                 235                 240

Ser Ala Leu Ser Lys Asp Pro Asn Glu Lys Arg Asp His Met Val Leu
                245                 250                 255

Leu Glu Phe Val Thr Ala Ala Gly Ile Thr Leu Gly Met Asp Glu Leu
                260                 265                 270

Tyr Lys Gly Gly Thr Gly Gly Ala Lys Val Val Ile Trp His Ala Met
                275                 280                 285

Gln Pro Asn Glu Leu Glu Val Phe Gln Ser Leu Ala Glu Glu Tyr Met
290                 295                 300

Ala Leu Cys Pro Glu Val Glu Ile Val Phe Glu Gln Lys Pro Asn Leu
305                 310                 315                 320

Glu Asp Ala Leu Lys Ala Ala Ile Pro Thr Gly Gln Gly Pro Asp Leu
                325                 330                 335

Phe Ile Trp Ala His Asp Trp Ile Gly Lys Phe Ala Glu Ala Gly Leu
                340                 345                 350

Leu Glu Pro Ile Asp Glu Tyr Val Thr Glu Asp Leu Leu Asn Glu Phe
                355                 360                 365

Ala Pro Met Ala Gln Asp Ala Met Gln Tyr Lys Gly His Tyr Tyr Ala
370                 375                 380

Leu Pro Phe Ala Ala Glu Thr Val Ala Ile Ile Tyr Ser Lys Glu Met
385                 390                 395                 400

Val Ser Glu Pro Pro Lys Thr Phe Asp Glu Met Lys Ala Ile Met Glu
                405                 410                 415

Lys Tyr Tyr Asp Pro Ala Asn Glu Lys Tyr Gly Ile Ala Trp Pro Ile
                420                 425                 430

Asn Ala Tyr Phe Ile Ser Ala Ile Ala Gln Ala Phe Gly Gly Tyr Tyr
                435                 440                 445

Phe Asp Asp Lys Thr Glu Gln Pro Gly Leu Asp Lys Pro Glu Thr Ile
                450                 455                 460

Glu Gly Phe Lys Phe Phe Thr Glu Ile Trp Pro Tyr Met Ala Pro
465                 470                 475                 480
```

```
Thr Gly Asp Tyr Asn Thr Gln Gln Ser Ile Phe Leu Glu Gly Arg Ala
            485                 490                 495
Pro Met Met Val Asn Gly Pro Trp Ser Ile Asn Asp Val Lys Lys Ala
        500                 505                 510
Gly Ile Asn Phe Gly Val Val Pro Leu Pro Ile Ile Lys Asp Gly
        515                 520                 525
Lys Glu Tyr Trp Pro Arg Pro Tyr Gly Gly Val Lys Leu Ile Tyr Phe
        530                 535                 540
Ala Ala Gly Ile Lys Asn Lys Asp Ala Ala Trp Lys Phe Ala Lys Trp
545                 550                 555                 560
Leu Thr Thr Ser Glu Glu Ser Ile Lys Thr Leu Ala Leu Glu Leu Gly
                565                 570                 575
Tyr Ile Pro Val Leu Thr Lys Val Leu Asp Asp Pro Glu Ile Lys Asn
                580                 585                 590
Asp Pro Val Ile Tyr Gly Phe Gly Gln Ala Val Gln His Ala Tyr Leu
                595                 600                 605
Met Pro Lys Ser Pro Lys Met Ser Ala Val Trp Gly Val Asp Gly
        610                 615                 620
Ala Ile Asn Glu Ile Leu Gln Asp Pro Gln Asn Ala Asp Ile Glu Gly
625                 630                 635                 640
Ile Leu Lys Lys Tyr Gln Gln Glu Ile Leu Asn Asn Met Gln Gly Thr
                645                 650                 655
Gly Gly Met Val Ser Lys Gly Glu Glu Leu Phe Thr Gly Val Val Pro
                660                 665                 670
Ile Leu Val Glu Leu Asp Gly Asp Val Asn Gly His Lys Phe Ser Val
                675                 680                 685
Ser Gly Glu Gly Glu Gly Asp Ala Thr Tyr Gly Lys Leu Thr Leu Lys
        690                 695                 700
Phe Ile Cys Thr Thr Gly Lys Leu Pro Val Pro Trp Pro Thr Leu Val
705                 710                 715                 720
Thr Thr Phe Gly Tyr Gly Leu Gln Cys Phe Ala Arg Tyr Pro Asp His
                725                 730                 735
Met Lys Gln His Asp Phe Phe Lys Ser Ala Met Pro Glu Gly Tyr Val
                740                 745                 750
Gln Glu Arg Thr Ile Phe Phe Lys Asp Asp Gly Asn Tyr Lys Thr Arg
        755                 760                 765
Ala Glu Val Lys Phe Glu Gly Asp Thr Leu Val Asn Arg Ile Glu Leu
        770                 775                 780
Lys Gly Ile Asp Phe Lys Glu Asp Gly Asn Ile Leu Gly His Lys Leu
785                 790                 795                 800
Glu Tyr Asn Tyr Asn Ser His Asn Val Tyr Ile Met Ala Asp Lys Gln
                805                 810                 815
Lys Asn Gly Ile Lys Val Asn Phe Lys Ile Arg His Asn Ile Glu Asp
                820                 825                 830
Gly Ser Val Gln Leu Ala Asp His Tyr Gln Gln Asn Thr Pro Ile Gly
        835                 840                 845
Asp Gly Pro Val Leu Leu Pro Asp Asn His Tyr Leu Ser Tyr Gln Ser
        850                 855                 860
Ala Leu Ser Lys Asp Pro Asn Glu Lys Arg Asp His Met Val Leu Leu
865                 870                 875                 880
Glu Phe Val Thr Ala Ala Gly Ile Thr Leu Gly Met Asp Glu Leu Tyr
                885                 890                 895
Lys
```

```
<210> SEQ ID NO 3
<211> LENGTH: 2685
<212> TYPE: DNA
<213> ORGANISM: Alicyclobacillus acidocaldarius
<220> FEATURE:
<221> NAME/KEY: CDS
<222> LOCATION: (1)..(2685)

<400> SEQUENCE: 3
```

| | | | | | | | | | | | | | | | | |
|---|---|---|---|---|---|---|---|---|---|---|---|---|---|---|---|---|
| atg | cgg | ggt | tct | cat | cat | cat | cat | cat | cat | ggt | atg | gct | agc | atg | act | 48 |
| Met | Arg | Gly | Ser | His | His | His | His | His | His | Gly | Met | Ala | Ser | Met | Thr | |
| 1 | | | | 5 | | | | | 10 | | | | | 15 | | |
| ggt | gga | cag | caa | atg | ggt | cgg | gat | ctg | tac | gac | gat | gac | gat | aag | gat | 96 |
| Gly | Gly | Gln | Gln | Met | Gly | Arg | Asp | Leu | Tyr | Asp | Asp | Asp | Asp | Lys | Asp | |
| | | 20 | | | | | 25 | | | | | 30 | | | | |
| ccg | ggc | cgc | atg | gtg | agc | aag | ggc | gag | gag | ctg | ttc | acc | ggg | gtg | gtg | 144 |
| Pro | Gly | Arg | Met | Val | Ser | Lys | Gly | Glu | Glu | Leu | Phe | Thr | Gly | Val | Val | |
| 35 | | | | | 40 | | | | | 45 | | | | | | |
| ccc | atc | ctg | gtc | gag | ctg | gac | ggc | gac | gta | aac | ggc | cac | aag | ttc | agc | 192 |
| Pro | Ile | Leu | Val | Glu | Leu | Asp | Gly | Asp | Val | Asn | Gly | His | Lys | Phe | Ser | |
| 50 | | | | | 55 | | | | | 60 | | | | | | |
| gtg | tcc | ggc | gag | ggc | gag | ggc | gat | gcc | acc | tac | ggc | aag | ctg | acc | ctg | 240 |
| Val | Ser | Gly | Glu | Gly | Glu | Gly | Asp | Ala | Thr | Tyr | Gly | Lys | Leu | Thr | Leu | |
| 65 | | | | 70 | | | | | 75 | | | | | 80 | | |
| aag | ttc | atc | tgc | acc | acc | ggc | aag | ctg | ccc | gtg | ccc | tgg | ccc | acc | ctc | 288 |
| Lys | Phe | Ile | Cys | Thr | Thr | Gly | Lys | Leu | Pro | Val | Pro | Trp | Pro | Thr | Leu | |
| | | | 85 | | | | | 90 | | | | | 95 | | | |
| gtg | acc | acc | ctg | acc | tgg | ggc | gtg | cag | tgc | ttc | agc | cgc | tac | ccc | gac | 336 |
| Val | Thr | Thr | Leu | Thr | Trp | Gly | Val | Gln | Cys | Phe | Ser | Arg | Tyr | Pro | Asp | |
| | | 100 | | | | | 105 | | | | | 110 | | | | |
| cac | atg | aag | cag | cac | gac | ttc | ttc | aag | tcc | gcc | atg | ccc | gaa | ggc | tac | 384 |
| His | Met | Lys | Gln | His | Asp | Phe | Phe | Lys | Ser | Ala | Met | Pro | Glu | Gly | Tyr | |
| | 115 | | | | | 120 | | | | | 125 | | | | | |
| gtc | cag | gag | cgc | acc | atc | ttc | ttc | aag | gac | gac | ggc | aac | tac | aag | acc | 432 |
| Val | Gln | Glu | Arg | Thr | Ile | Phe | Phe | Lys | Asp | Asp | Gly | Asn | Tyr | Lys | Thr | |
| | 130 | | | | | 135 | | | | | 140 | | | | | |
| cgc | gcc | gag | gtg | aag | ttc | gag | ggc | gac | acc | ctg | gtg | aac | cgc | atc | gag | 480 |
| Arg | Ala | Glu | Val | Lys | Phe | Glu | Gly | Asp | Thr | Leu | Val | Asn | Arg | Ile | Glu | |
| 145 | | | | | 150 | | | | | 155 | | | | | 160 | |
| ctg | aag | ggc | atc | gac | ttc | aag | gag | gac | ggc | aac | atc | ctg | ggg | cac | aag | 528 |
| Leu | Lys | Gly | Ile | Asp | Phe | Lys | Glu | Asp | Gly | Asn | Ile | Leu | Gly | His | Lys | |
| | | | | 165 | | | | | 170 | | | | | 175 | | |
| ctg | gag | tac | aac | tac | atc | agc | cac | aac | gtc | tat | atc | acc | gcc | gac | aag | 576 |
| Leu | Glu | Tyr | Asn | Tyr | Ile | Ser | His | Asn | Val | Tyr | Ile | Thr | Ala | Asp | Lys | |
| | | | | 180 | | | | | 185 | | | | | 190 | | |
| cag | aag | aac | ggc | atc | aag | gcc | aac | ttc | aag | atc | cgc | cac | aac | atc | gag | 624 |
| Gln | Lys | Asn | Gly | Ile | Lys | Ala | Asn | Phe | Lys | Ile | Arg | His | Asn | Ile | Glu | |
| | | | 195 | | | | | 200 | | | | | 205 | | | |
| gac | ggc | agc | gtg | cag | ctc | gcc | gac | cac | tac | cag | cag | aac | acc | ccc | atc | 672 |
| Asp | Gly | Ser | Val | Gln | Leu | Ala | Asp | His | Tyr | Gln | Gln | Asn | Thr | Pro | Ile | |
| | 210 | | | | | 215 | | | | | 220 | | | | | |
| ggc | gac | ggc | ccc | gtg | ctg | ctg | ccc | gac | aac | cac | tac | ctg | agc | acc | cag | 720 |
| Gly | Asp | Gly | Pro | Val | Leu | Leu | Pro | Asp | Asn | His | Tyr | Leu | Ser | Thr | Gln | |
| 225 | | | | | 230 | | | | | 235 | | | | | 240 | |
| tcc | gcc | ctg | agc | aaa | gac | ccc | aac | gag | aag | cgc | gat | cac | atg | gtc | ctg | 768 |
| Ser | Ala | Leu | Ser | Lys | Asp | Pro | Asn | Glu | Lys | Arg | Asp | His | Met | Val | Leu | |
| | | | | 245 | | | | | 250 | | | | | 255 | | |
| ctg | gag | ttc | gtg | acc | gcc | gcc | ggg | atc | act | gat | atc | aca | agt | ttg | tac | 816 |
| Leu | Glu | Phe | Val | Thr | Ala | Ala | Gly | Ile | Thr | Asp | Ile | Thr | Ser | Leu | Tyr | |
| | | | | 260 | | | | | 265 | | | | | 270 | | |
| aaa | aaa | gca | ggc | tcg | cag | acc | atc | acc | gtt | tgg | tcg | tgg | cag | aca | ggg | 864 |

```
        Lys Lys Ala Gly Ser Gln Thr Ile Thr Val Trp Ser Trp Gln Thr Gly
            275                 280                 285 ccg gag ttg caa gac gtg aag cag atc gcc gct cag tgg gca aag gct        912
Pro Glu Leu Gln Asp Val Lys Gln Ile Ala Ala Gln Trp Ala Lys Ala
        290                 295                 300 cat ggg gac aag gtc att gtc gtc gac caa agc tcc aat ccg aag gga        960
His Gly Asp Lys Val Ile Val Val Asp Gln Ser Ser Asn Pro Lys Gly
305                 310                 315                 320 ttc cag ttc tac gcc acg gcg gct cgc acg ggc aag ggg cct gat gtc       1008
Phe Gln Phe Tyr Ala Thr Ala Ala Arg Thr Gly Lys Gly Pro Asp Val
                325                 330                 335 gtg ttt gga atg ccg cac gac aat aat ggc gtt ttc gca gaa gaa gga       1056
Val Phe Gly Met Pro His Asp Asn Asn Gly Val Phe Ala Glu Glu Gly
            340                 345                 350 ttg atg gcg ccg gta ccg tct ggc gtg ctc aac acg ggt ctc tat gca       1104
Leu Met Ala Pro Val Pro Ser Gly Val Leu Asn Thr Gly Leu Tyr Ala
        355                 360                 365 cct aat acg atc gac gcc atc aag gtc aac ggc acg atg tac tcg gtg       1152
Pro Asn Thr Ile Asp Ala Ile Lys Val Asn Gly Thr Met Tyr Ser Val
370                 375                 380 cca gta tcc gtt cag gtc gcg gca atc tac tac aac aaa aag ctt gtg       1200
Pro Val Ser Val Gln Val Ala Ala Ile Tyr Tyr Asn Lys Lys Leu Val
385                 390                 395                 400 ccg cag cca ccg cag aca tgg gcc gaa ttc gtg aaa gac gca aat gca       1248
Pro Gln Pro Pro Gln Thr Trp Ala Glu Phe Val Lys Asp Ala Asn Ala
                405                 410                 415 cat ggc ttc atg tat gac caa gcg aat ctt tac ttc gat tac gcc att       1296
His Gly Phe Met Tyr Asp Gln Ala Asn Leu Tyr Phe Asp Tyr Ala Ile
            420                 425                 430 atc ggc ggc tat ggc ggg tat gtg ttc aag gac aac aac ggc aca ctc       1344
Ile Gly Gly Tyr Gly Gly Tyr Val Phe Lys Asp Asn Asn Gly Thr Leu
        435                 440                 445 gac ccg aac aac ata ggt ctt gac aca ccg ggg gct gtg cag gct tac       1392
Asp Pro Asn Asn Ile Gly Leu Asp Thr Pro Gly Ala Val Gln Ala Tyr
450                 455                 460 acg ctg atg agg gat atg gtc tcc aag tat cac tgg atg acc ccg agc       1440
Thr Leu Met Arg Asp Met Val Ser Lys Tyr His Trp Met Thr Pro Ser
465                 470                 475                 480 acg aat ggc tct atc gcg aag gct gag ttt ctg gct ggg aag att ggt       1488
Thr Asn Gly Ser Ile Ala Lys Ala Glu Phe Leu Ala Gly Lys Ile Gly
                485                 490                 495 atg tac gtg agt ggc cca tgg gac acg gcg gat att gag aag gcc aaa       1536
Met Tyr Val Ser Gly Pro Trp Asp Thr Ala Asp Ile Glu Lys Ala Lys
            500                 505                 510 att gac ttc ggt gta acg cca tgg ccc acc ttg ccg aac ggc aag cat       1584
Ile Asp Phe Gly Val Thr Pro Trp Pro Thr Leu Pro Asn Gly Lys His
        515                 520                 525 gcc acg ccc ttc tta ggc gtt atc acg gca ttt gtg aac aag gag tcc       1632
Ala Thr Pro Phe Leu Gly Val Ile Thr Ala Phe Val Asn Lys Glu Ser
530                 535                 540 aag acc cag gca gct gac tgg agc ctt gtt caa gcg ttg acc agt gcg       1680
Lys Thr Gln Ala Ala Asp Trp Ser Leu Val Gln Ala Leu Thr Ser Ala
545                 550                 555                 560 cag gcg cag caa atg tac ttc aga gat tcc cag cag att cct gcg ctc       1728
Gln Ala Gln Gln Met Tyr Phe Arg Asp Ser Gln Gln Ile Pro Ala Leu
                565                 570                 575 ttg tct gtg cag agg tcg agc gcc gtc cag tcg agc cca acc ttt aaa       1776
Leu Ser Val Gln Arg Ser Ser Ala Val Gln Ser Ser Pro Thr Phe Lys
            580                 585                 590 gcg ttc gtc gaa cag ttg cgc tac gcg gta ccg atg ccc aac att ccg       1824
```

```
                Ala Phe Val Glu Gln Leu Arg Tyr Ala Val Pro Met Pro Asn Ile Pro
                            595                 600                 605 caa atg cag gcc gtg tgg caa gca atg agc atc ctg cag aat atc att       1872
Gln Met Gln Ala Val Trp Gln Ala Met Ser Ile Leu Gln Asn Ile Ile
610                 615                 620 gcg ggc aag gtg tca cca gag cag ggt gcg aag gat ttt gtg caa aac       1920
Ala Gly Lys Val Ser Pro Glu Gln Gly Ala Lys Asp Phe Val Gln Asn
625                 630                 635                 640 att caa aaa ggc atc aac cca gct ttc ttg tac aaa gtg gta ata tcg       1968
Ile Gln Lys Gly Ile Asn Pro Ala Phe Leu Tyr Lys Val Val Ile Ser
                645                 650                 655 gtg agc aag ggc gag gag ctg ttc acc ggg gtg gtg ccc atc ctg gtc       2016
Val Ser Lys Gly Glu Glu Leu Phe Thr Gly Val Val Pro Ile Leu Val
            660                 665                 670 gag ctg gac ggc gac gta aac ggc cac aag ttc agc gtg tcc ggc gag       2064
Glu Leu Asp Gly Asp Val Asn Gly His Lys Phe Ser Val Ser Gly Glu
        675                 680                 685 ggc gag ggc gat gcc acc tac ggc aag ctg acc ctg aag ttc atc tgc       2112
Gly Glu Gly Asp Ala Thr Tyr Gly Lys Leu Thr Leu Lys Phe Ile Cys
    690                 695                 700 acc acc ggc aag ctg ccc gtg ccc tgg ccc acc ctc gtg acc acc ttc       2160
Thr Thr Gly Lys Leu Pro Val Pro Trp Pro Thr Leu Val Thr Thr Phe
705                 710                 715                 720 ggc tac ggc ctg cag tgc ttc gcc cgc tac ccc gac cac atg aag cag       2208
Gly Tyr Gly Leu Gln Cys Phe Ala Arg Tyr Pro Asp His Met Lys Gln
                725                 730                 735 cac gac ttc ttc aag tcc gcc atg ccc gaa ggc tac gtc cag gag cgc       2256
His Asp Phe Phe Lys Ser Ala Met Pro Glu Gly Tyr Val Gln Glu Arg
            740                 745                 750 acc atc ttc ttc aag gac gac ggc aac tac aag acc cgc gcc gag gtg       2304
Thr Ile Phe Phe Lys Asp Asp Gly Asn Tyr Lys Thr Arg Ala Glu Val
        755                 760                 765 aag ttc gag ggc gac acc ctg gtg aac cgc atc gag ctg aag ggc atc       2352
Lys Phe Glu Gly Asp Thr Leu Val Asn Arg Ile Glu Leu Lys Gly Ile
    770                 775                 780 gac ttc aag gag gac ggc aac atc ctg ggg cac aag ctg gag tac aac       2400
Asp Phe Lys Glu Asp Gly Asn Ile Leu Gly His Lys Leu Glu Tyr Asn
785                 790                 795                 800 tac aac agc cac aac gtc tat atc atg gcc gac aag cag aag aac ggc       2448
Tyr Asn Ser His Asn Val Tyr Ile Met Ala Asp Lys Gln Lys Asn Gly
                805                 810                 815 atc aag gtg aac ttc aag atc cgc cac aac atc gag gac ggc agc gtg       2496
Ile Lys Val Asn Phe Lys Ile Arg His Asn Ile Glu Asp Gly Ser Val
            820                 825                 830 cag ctc gcc gac cac tac cag cag aac acc ccc atc ggc gac ggc ccc       2544
Gln Leu Ala Asp His Tyr Gln Gln Asn Thr Pro Ile Gly Asp Gly Pro
        835                 840                 845 gtg ctg ctg ccc gac aac cac tac ctg agc tac cag tcc gcc ctg agc       2592
Val Leu Leu Pro Asp Asn His Tyr Leu Ser Tyr Gln Ser Ala Leu Ser
    850                 855                 860 aaa gac ccc aac gag aag cgc gat cac atg gtc ctg ctg gag ttc gtg       2640
Lys Asp Pro Asn Glu Lys Arg Asp His Met Val Leu Leu Glu Phe Val
865                 870                 875                 880 acc gcc gcc ggg atc act ctc ggc atg gac gag ctg tac aag taa           2685
Thr Ala Ala Gly Ile Thr Leu Gly Met Asp Glu Leu Tyr Lys
                885                 890

<210> SEQ ID NO 4
<211> LENGTH: 894
<212> TYPE: PRT
<213> ORGANISM: Alicyclobacillus acidocaldarius
```

<400> SEQUENCE: 4

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Gly Arg Met Val Ser Lys Gly Glu Glu Leu Phe Thr Gly Val Val
            35                  40                  45

Pro Ile Leu Val Glu Leu Asp Gly Asp Val Asn Gly His Lys Phe Ser
50                  55                  60

Val Ser Gly Glu Gly Glu Gly Asp Ala Thr Tyr Gly Lys Leu Thr Leu
65                  70                  75                  80

Lys Phe Ile Cys Thr Thr Gly Lys Leu Pro Val Pro Trp Pro Thr Leu
                85                  90                  95

Val Thr Thr Leu Thr Trp Gly Val Gln Cys Phe Ser Arg Tyr Pro Asp
            100                 105                 110

His Met Lys Gln His Asp Phe Phe Lys Ser Ala Met Pro Glu Gly Tyr
            115                 120                 125

Val Gln Glu Arg Thr Ile Phe Phe Lys Asp Asp Gly Asn Tyr Lys Thr
130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Ile Ser His Asn Val Tyr Ile Thr Ala Asp Lys
            180                 185                 190

Gln Lys Asn Gly Ile Lys Ala Asn Phe Lys Ile Arg His Asn Ile Glu
            195                 200                 205

Asp Gly Ser Val Gln Leu Ala Asp His Tyr Gln Gln Asn Thr Pro Ile
210                 215                 220

Gly Asp Gly Pro Val Leu Leu Pro Asp Asn His Tyr Leu Ser Thr Gln
225                 230                 235                 240

Ser Ala Leu Ser Lys Asp Pro Asn Glu Lys Arg Asp His Met Val Leu
                245                 250                 255

Leu Glu Phe Val Thr Ala Ala Gly Ile Thr Asp Ile Thr Ser Leu Tyr
            260                 265                 270

Lys Lys Ala Gly Ser Gln Thr Ile Thr Val Trp Ser Trp Gln Thr Gly
            275                 280                 285

Pro Glu Leu Gln Asp Val Lys Gln Ile Ala Ala Gln Trp Ala Lys Ala
290                 295                 300

His Gly Asp Lys Val Ile Val Val Asp Gln Ser Ser Asn Pro Lys Gly
305                 310                 315                 320

Phe Gln Phe Tyr Ala Thr Ala Ala Arg Thr Gly Lys Gly Pro Asp Val
                325                 330                 335

Val Phe Gly Met Pro His Asp Asn Asn Gly Val Phe Ala Glu Glu Gly
            340                 345                 350

Leu Met Ala Pro Val Pro Ser Gly Val Leu Asn Thr Gly Leu Tyr Ala
            355                 360                 365

Pro Asn Thr Ile Asp Ala Ile Lys Val Asn Gly Thr Met Tyr Ser Val
370                 375                 380

Pro Val Ser Val Gln Val Ala Ala Ile Tyr Tyr Asn Lys Lys Leu Val
385                 390                 395                 400

Pro Gln Pro Pro Gln Thr Trp Ala Glu Phe Val Lys Asp Ala Asn Ala
                405                 410                 415
```

-continued

```
His Gly Phe Met Tyr Asp Gln Ala Asn Leu Tyr Phe Asp Tyr Ala Ile
            420                 425                 430
Ile Gly Gly Tyr Gly Tyr Val Phe Lys Asp Asn Asn Gly Thr Leu
            435                 440                 445
Asp Pro Asn Asn Ile Gly Leu Asp Thr Pro Gly Ala Val Gln Ala Tyr
450                 455                 460
Thr Leu Met Arg Asp Met Val Ser Lys Tyr His Trp Met Thr Pro Ser
465                 470                 475                 480
Thr Asn Gly Ser Ile Ala Lys Ala Glu Phe Leu Ala Gly Lys Ile Gly
            485                 490                 495
Met Tyr Val Ser Gly Pro Trp Asp Thr Ala Asp Ile Glu Lys Ala Lys
            500                 505                 510
Ile Asp Phe Gly Val Thr Pro Trp Pro Thr Leu Pro Asn Gly Lys His
            515                 520                 525
Ala Thr Pro Phe Leu Gly Val Ile Thr Ala Phe Val Asn Lys Glu Ser
            530                 535                 540
Lys Thr Gln Ala Ala Asp Trp Ser Leu Val Gln Ala Leu Thr Ser Ala
545                 550                 555                 560
Gln Ala Gln Gln Met Tyr Phe Arg Asp Ser Gln Ile Pro Ala Leu
            565                 570                 575
Leu Ser Val Gln Arg Ser Ser Ala Val Gln Ser Ser Pro Thr Phe Lys
            580                 585                 590
Ala Phe Val Glu Gln Leu Arg Tyr Ala Val Pro Met Pro Asn Ile Pro
            595                 600                 605
Gln Met Gln Ala Val Trp Gln Ala Met Ser Ile Leu Gln Asn Ile Ile
            610                 615                 620
Ala Gly Lys Val Ser Pro Glu Gln Gly Ala Lys Asp Phe Val Gln Asn
625                 630                 635                 640
Ile Gln Lys Gly Ile Asn Pro Ala Phe Leu Tyr Lys Val Val Ile Ser
            645                 650                 655
Val Ser Lys Gly Glu Glu Leu Phe Thr Gly Val Val Pro Ile Leu Val
            660                 665                 670
Glu Leu Asp Gly Asp Val Asn Gly His Lys Phe Ser Val Ser Gly Glu
            675                 680                 685
Gly Glu Gly Asp Ala Thr Tyr Gly Lys Leu Thr Leu Lys Phe Ile Cys
            690                 695                 700
Thr Thr Gly Lys Leu Pro Val Pro Trp Pro Thr Leu Val Thr Thr Phe
705                 710                 715                 720
Gly Tyr Gly Leu Gln Cys Phe Ala Arg Tyr Pro Asp His Met Lys Gln
            725                 730                 735
His Asp Phe Phe Lys Ser Ala Met Pro Glu Gly Tyr Val Gln Glu Arg
            740                 745                 750
Thr Ile Phe Phe Lys Asp Asp Gly Asn Tyr Lys Thr Arg Ala Glu Val
            755                 760                 765
Lys Phe Glu Gly Asp Thr Leu Val Asn Arg Ile Glu Leu Lys Gly Ile
            770                 775                 780
Asp Phe Lys Glu Asp Gly Asn Ile Leu Gly His Lys Leu Glu Tyr Asn
785                 790                 795                 800
Tyr Asn Ser His Asn Val Tyr Ile Met Ala Asp Lys Gln Lys Asn Gly
            805                 810                 815
Ile Lys Val Asn Phe Lys Ile Arg His Asn Ile Glu Asp Gly Ser Val
            820                 825                 830
Gln Leu Ala Asp His Tyr Gln Gln Asn Thr Pro Ile Gly Asp Gly Pro
```

-continued

```
                835                 840                 845
Val Leu Leu Pro Asp Asn His Tyr Leu Ser Tyr Gln Ser Ala Leu Ser
    850                 855                 860

Lys Asp Pro Asn Glu Lys Arg Asp His Met Val Leu Leu Glu Phe Val
865                 870                 875                 880

Thr Ala Ala Gly Ile Thr Leu Gly Met Asp Glu Leu Tyr Lys
                885                 890
```

ENVIRONMENTALLY STABLE SENSORS AND METHODS OF USING THE SAME

CROSS-REFERENCE TO RELATED APPLICATIONS

The present application is a U.S. National Phase Application of International Application No. PCT/US2005/036954, filed Oct. 14, 2005, which claims the benefit of U.S. Provisional Application No. 60/658,142, filed Mar. 4, 2005, both of which are hereby incorporated by reference in their entireties.

This application is also related to provisional application Ser. No. 60/643,576, provisional application Ser. No. 60/658,141, provisional application Ser. No. 60/657,702, PCT application [PCT/US2005036955, filed Oct. 14, 2005, "Phosphate Biosensors and Methods of Using the Same"], PCT application [PCT/US2005/036953, filed Oct. 14, 2005, "Methods of Reducing Repeat-Induced Silencing of Transgene Expression and Improved Fluorescent Biosensors"] and PCT application [PCT/US2005036951, filed Oct. 14, 2005, "Sucrose Biosensors and Methods of Using the Same"], which are herein incorporated by reference in their entireties.

STATEMENT REGARDING FEDERALLY SPONSORED RESEARCH OR DEVELOPMENT

This invention was funded through NIH grant No. 1R33 DK070272-01, an NIH subcontract from Duke University (Subcontract No. SPSID 126632) and a Human Frontier Science Program grant (Contract No. RGP0041/2004C). Accordingly, the U.S. Government has certain rights to this invention.

FIELD OF INVENTION

The invention relates generally to the field of construction of environmentally stable biosensors and methods for measuring and detecting changes in metabolite levels using fluorescence resonance energy transfer (FRET).

BACKGROUND OF INVENTION

All publications and patent applications herein are incorporated by reference to the same extent as if each individual publication or patent application was specifically and individually indicated to be incorporated by reference.

The publications discussed herein are provided solely for their disclosure prior to the filing date of the present application. Nothing herein is to be construed as an admission that the present invention is not entitled to antedate such publication by virtue of prior invention.

Hyperthermophilic organisms, i.e. organisms which thrive on temperatures around the boiling point of water (which may be significantly above 100° C. at high pressures), are found primarily in the depths of the ocean close to geothermal springs, but also occur in many other natural and artificial environments. Since these bacteria live in high temperature environments, their enzymes, which are essential to sustaining life processes such as digestion and respiration, must be able to function at such extreme temperature conditions. Enzymes in common mesophilic bacteria (i.e., organisms that can grow at intermediate temperatures compared to the upper and lower extremes for all organisms) typically fail at these high temperatures.

A number of organisms have been isolated from extreme environments. These organisms have been studied and certain useful compounds have been identified. For example, thermostable DNA polymerases have been obtained from *Thermus aquaticus*. Proteases have been isolated from thermophiles including *T. aquaticus, Desulfurococcus* species, *Pyrococcus furiosus, Sulfolobus acidocaldarius, Thermococcus stetteri, Thermus thermophilus*, and *Pyrobaculum aerophilum*. However, difficulties in culturing extremophiles have limited the number of these microbes which have been characterized as well as the number of useful compounds isolated therefrom (Brennan, Chemical and Engineering News, Oct. 14, 1996). The new practice of metagenome cloning may circumvent these culturing issues in the future (Rhee, J. K. et al. "New thermophilic and thermostable esterase with sequence similarity to the hormone-sensitive lipase family, cloned from a metagenomic library", Appl. Environ. Microbiol. 71 (2): 817-825).

Stetter, et al. identified microorganisms from the hot springs of Vulcano Island, Italy, that flourish at temperatures exceeding 100° C. (Stetter, K. O. "Microbial Life in Hyperthermal Environments," ASM News 61:285-290, 1995; Stetter, K. O., Fiala, G., Huber, R. And Segerer, A. "Hyperthermophilic Microorganisms," FEMS Microbiol. Rev. 75:117-124, 1990). While thermophilic organisms that grow optimally at 60° C. have been known for many years, the hyperthermophilic (or extremely thermophilic) microorganisms belong to a new evolutionary class called Archaea (Woese, C. R., Kandler, O. and Wheelis, M. L. "Towards a Natural System of Organisms: Proposal for the Domains Archaea, Bacteria, and Eucarya," Proc. Natl. Acad. Sci. USA 87:4576-4579, 1990). The Archaea are believed to have originated over a billion years ago during the epoch when the Earth was cooling. Consequently their evolutionary development was set in motion within the environment of hot springs and deep sea hydrothermal vents. One member of this new group is *Pyrococcus furiosus*.

Hyperthermophilic organisms such as *Pyrococcus furiosus* have evolved to survive at significantly elevated temperatures. To accomplish this, the bacterial proteins, particularly those expressed in the periplasmic space (where the contact with the environment is most felt), must be well-adapted to these conditions. *Pyrococcus furiosus* is an obligate heterotroph that can be grown on polymeric substrates including protein and starch at temperatures of up to about 103° C. Preparations containing proteolytic enzymes prepared from *Pyrococcus furiosus* have been previously described in U.S. Pat. Nos. 5,242,817 and 5,391,489. See also, for example, Blumentals, Ilse I., Robinson, Anne S., and Kelly, Robert M., "Characterization of Sodium Dodecyl Sulfate-Resistant Proteolytic Activity in the Hyperthermophilic Archaebacterium *Pyrococcus furiosus*." Applied and Environmental Microbiology, 56, 7:1992-1998, (1990); Eggen, Rik, Geerling, Ans, Watts, Jennifer and de Vos, Willem M., "Characterization of pyrolysin, a hyperthermoactive serine protease from the archaebacterium *Pyrococcus furiosus*." FEMS Microbiology Letters, 71:17-20 (1990); Voorhorst, Wilfried G. B., Eggen, Rik I. L., Geerling, Ans C. M., Platteeuw, Christ, Siezen, Roland J., de Vos, Willem M., "Isolation and Characterization of the Hyperthermostable Serine Protease, Pyrolysin, and Its Gene from the Hyperthermophilic Archaeon *Pyrococcus furiosus*." Journal of Biological Chemistry, 271, 34: 20426-20431 (1996).

In the past several years, there have been several thermophilic eukaryotic organisms discovered as well, e.g. the Pompeii worm *Alvinella pompejana*, which thrives in a temperature gradient of 20-80° C., in a very low pH and high heavy metal environment. Another thermo-acidophilic species, *Alicyclobacillus acidocaldarius*, has evolved to live at elevated temperatures and extremely low pH. For this reason, it is thought that proteins from this organism (particularly periplasmic proteins, exposed to the full brunt of extreme environmental conditions) should be able to function as sensors in such environments, which might be seen locally in such parts of the cell as the vacuole.

Concurrent to the discovery of the ever increasing number of hyperthermophilic species in recent years, in vivo measurement of ions and metabolites by using Fluorescence Resonance Energy Transfer (FRET) has been successfully used. For instance, the FRET technology has been used to measure calcium concentration changes, by fusing CFP, YFP, and a recognition domain consisting of calmodulin and the M13 peptide (Zhang, J., Campbell, R. E., Ting, A. Y., and Tsien, R. Y. (2002a) Creating new fluorescent probes for cell biology. Nat Rev Mol Cell Biol 3, 906-918; Zhang, J., Campbell, R. E., Ting, A. Y., and Tsien, R. Y. (2002b) Creating new fluorescent probes for cell biology. Nature Reviews Molecular Cell Biology 3, 906-918). Binding of calcium to calmodulin causes global structural rearrangement of the chimera resulting in a change in FRET intensity as mediated by the donor and acceptor fluorescent moieties. Recently a number of bacterial periplasmic binding proteins, which undergo a Venus flytrap-like closure of two lobes upon substrate binding, have been successfully used as the scaffold for metabolite nanosensors (Fehr, M., Frommer, W. B., and Lalonde, S. (2002) Visualization of maltose uptake in living yeast cells by fluorescent nanosensors. Proc. Natl. Acad. Sci. U S A 99, 9846-9851; Fehr, M., Lalonde, S., Lager, I., Wolff, M. W., and Frommer, W. B. (2003) In vivo imaging of the dynamics of glucose uptake in the cytosol of COS-7 cells by fluorescent nanosensors. J. Biol. Chem. 278, 19127-19133; Lager, I., Fehr, M., Frommer, W. B., and Lalonde, S. (2003) Development of a fluorescent nanosensor for ribose. FEBS Lett 553, 85-89).

Although FRET biosensors have proved to be indispensable tools in the study of metabolite levels in the living organisms, the construction of the biosensors with mesophilic ligand binding proteins has its limits. One of the limits is that the ligand binding proteins may become destabilized once mutations are introduced into the protein via protein engineering, e.g. to alter ligand-binding specificity or improve the sensor signal. For instance, a putative lactate-binding protein Lac.G2 (Looger et al., Nature, 423 (6936): 185-190) was constructed by mutation of FLIP-mglB.Ec, and although it showed evidence of lactate binding, it was significantly destabilized, as evidenced by the temperature-dependent decrease in FRET signal. It is therefore necessary to develop environmentally stable biosensors with improved thermo-, chemo-, and acido-stablity, which may provide more robust scaffolds for protein engineering.

Therefore, a need exists for improved environmentally stable biosensors which can be easily produced.

SUMMARY OF INVENTION

The present invention is based on the concept that thermophilic proteins appear to possess favorable enthalpic and entropic contributions to $\Delta G_{fold}$, and may provide a more robust platform for nanosensor construction and engineering. These highly evolved proteins will almost certainly give rise to more rugged recognition elements of sensors, and furthermore may accommodate a higher degree of mutagenesis while still providing a folded and stable protein. This latter property will be of utility for the re-design of these proteins to bind to other ligands. It will also assist in the construction of loop-inserted FLIP constructs, which although typically possessing a higher signal-to-noise ratio versus a linear, terminal fusion, are also typically destabilized in comparison.

The FRET biosensors described in the present application are the first reduction of this concept to practice. For instance, the FRET biosensors constructed using *Pyrococcus furiosus* malE or *Alicyclobacillus acidocaldarius* malE as described herein show the expected maltose binding, a good signal change, robust resistance to guanidinium hydrochloride denaturation, and a more pH-stable signal than the mesophilic protein FLIP-malE.Ec construct prepared using *Escherichia coli* malE. Biosensors comprising other thermophilic protein binding domains, for instance from *Pyrococcus furiosus*, *Alicyclobacillus acidocaldarius* or other thermophilic organisms, can also be generated using the methods described herein.

The present invention thus provides environmentally stable biosensors that are resistant to acid-, thermal- and chemical denaturation, utilizing hyperthermophilic and thermophilic proteins for detecting and measuring changes in metabolite concentrations. In particular, the invention provides an isolated nucleic acid sequence which encodes an environmentally stable fluorescent indicator, the indicator comprising a ligand binding protein moiety from a thermophilic organism, a donor fluorophore moiety covalently coupled to the ligand-binding protein moiety, and an acceptor fluorophore moiety covalently coupled to the ligand-binding protein moiety, wherein fluorescence resonance energy transfer (FRET) between the donor moiety and the acceptor moiety is altered when the donor moiety is excited and ligand binds to the ligand-binding protein moiety. Vectors, including expression vectors, and host cells comprising the inventive nucleic acids are also provided, as well as biosensor proteins encoded by the nucleic acids. Such nucleic acids, vectors, host cells and proteins may be used in methods of detecting ligand binding and changes in levels of analytes, and in methods of identifying compounds that modulate ligand binding.

BRIEF DESCRIPTION OF THE DRAWINGS

FIG. 1, comprising

FIG. 2, comprising

FIG. 3 compares the resistance of malE_Pf, MalE_Aa, and MalE_Ec nanosensors to thermal denaturation at 70° C. (FIG. 3e), 90° C. (FIG. 3f) and 95° C. (FIG. 3g).

DETAILED DESCRIPTION OF INVENTION

Figure 1A:
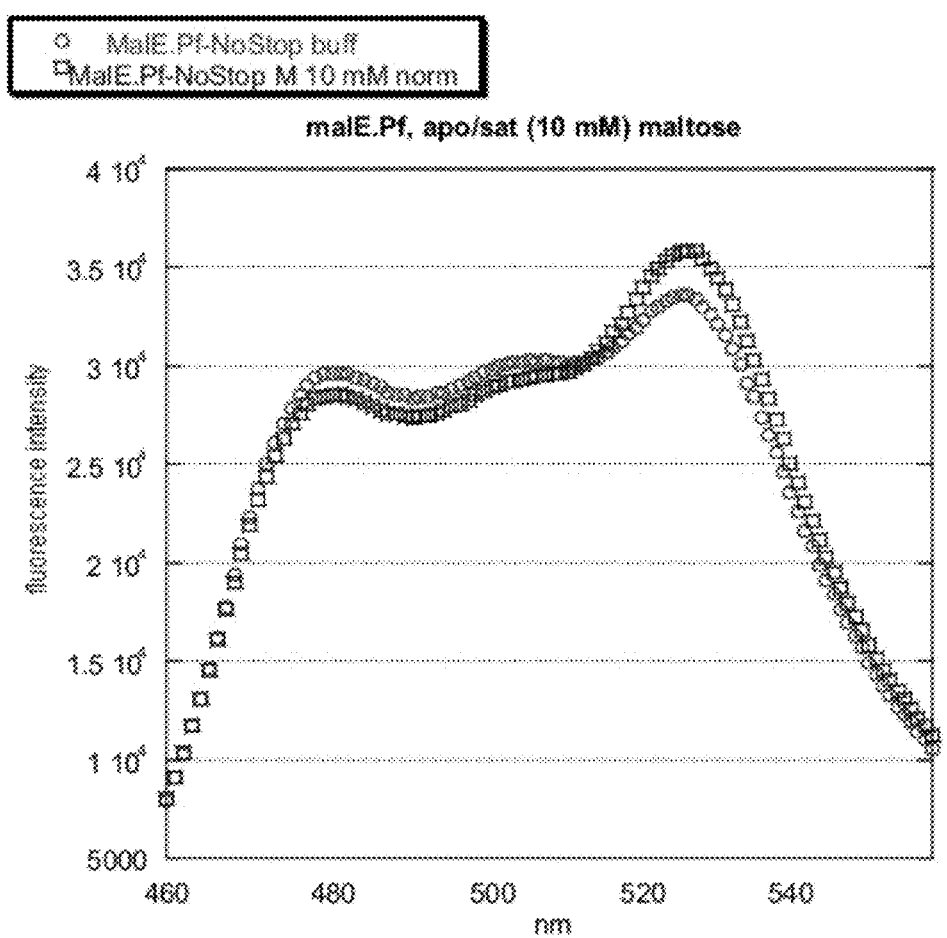
FIGS. 1a and 1b, shows signal changes of nanosensors of malE_Pf and malE_Aa in the presence or absence of 10 mM maltose.

The following description includes information that may be useful in understanding the present invention. It is not an admission that any of the information provided herein is prior art or relevant to the presently claimed inventions, or that any publication specifically or implicitly referenced is prior art.

Other objects, advantages and features of the present invention become apparent to one skilled in the art upon reviewing the specification and the drawings provided herein.

Thus, further objects and advantages of the present invention will be clear from the description that follows.

Biosensors

The present invention provides environmentally stable biosensors utilizing hyperthermophilic and moderately thermophilic proteins for detecting and measuring changes in target biological metabolite concentrations using Fluorescence Resonance Energy Transfer (FRET). As used herein, "thermophilic" refers to both hyperthermophilic (or extreme thermophilic) and moderately thermophilic proteins and organisms as further described below. "Environmentally stable" in the context of the present invention is used to indicate that the biosensors are resistant to acid, thermal, and/or chemical denaturation. For instance, such acids may include, but are not limited to, HCl. The resistance temperature may be above 50, 60, 70, 80, 90, 100, or 110° C. Such chemical denaturants may include, but are not limited to guanidinium hydrochloride, urea, Triton X-100, and sodium dodecyl sulfate.

In one embodiment, among others, the invention provides fluorescent indicators comprising a ligand-binding protein from a hyperthermophilic organism, particularly indicators comprising a maltose/maltodextrin-binding protein moiety from *Pyrococcus furiosus* or *Alicyclobacillus acidocaldarius* maltose/maltodextrin-binding protein. However, the present invention is not limited by any particular ligand-binding protein, or by any particular hyperthermophilic or thermophilic organism. Rather, the present invention includes FRET biosensors comprising any ligand-binding proteins that can be identified in a thermophilic organism, including hyperthermophilic organisms or moderate thermophilic organisms.

As used herein, "hyperthermophilic" or "extreme thermophilic" refers to a general term for organisms which have a temperature range of growth which falls within the range of about 65 to about 115° C. Hyperthermophilic is sometimes also used herein to refer to enzymes produced by hyperthermophilic organisms. For example *S. solfataricus* has a temperature range of growth of about 65° C. to about 91° C. Suitable hyperthermophilic organisms include, but are not limited to, bacterial species of *Thermus, Thermocrinis, Thermatoga, Thermoplasma, Thermococcus, Thermoactinomyces, Aquifex, Aeropyrem, Archeoglobus, Pyrococcus, Pyrolobus, Acidianus* and *Sulfolobus*, including for instance *Thermus aquaticus, Thermus thermophilus, Thermus brockianus, Thermus flavus, Thermocrinis ruber, Thermatoga maritima, Thermatoga thermarum, Thermatoga neapolitana, Thermococcus litoralis, Pyrococcus furiosus, Pyrococcus woesii, Pyrolobus fumarii*. Also included are the thermophilic eukaryotic organisms including, but not limited to, *Alvinella pompejana* and *Cyanidium caldarium*.

As used herein, "moderate thermophile" refers to a general term for microorganisms which have a temperature range of growth which falls within the range of about 45 to 65° C. Suitable moderate thermophile organisms may, for example, be selected from the group consisting of species of *Acidithiobacillus, Acidimicrobium, Sulfobacillus, Ferroplasma, Thermoplasma* and *Alicyclobacillus*, including, for instance, *Acidithiobacillus caldus* (formerly *Thiobacillus caldus*); *Acidimicrobium ferrooxidans; Sulfobacillus acidophilus; Sulfobacillus disulfidooxidans; Sulfobacillus thermosulfidooxidans; Ferroplasma acidarmanus; Thermoplasma acidophilum*; and *Alicyclobacillus acidocaldarius. Alicyclobacillus acidocaldarius* are both thermo- and acidostable. The structure of its thermoacidostable maltose-binding protein has been elucidated by X-ray and the protein has been shown to be tolerant to low pH (Hulsmann et al., (2000) Maltose and maltodextrin transport in the thermoacidophilic gram-positive bacterium *Alicyclobacillus acidocaldarius* is mediated by a high-affinity transport system that includes a maltose binding protein tolerant to low pH. J. Bacteriol. 182, 6292-6301; Schafer et al., (2004) X-ray structures of the maltose-maltodextrin-binding protein of the thermoacidophilic bacterium *Alicyclobacillus acidocaldarius* provide insight into acid stability of proteins. J. Mol. Biol. 335, 261-274).

Thus, the invention provides isolated nucleic acids encoding fluorescent indicators constructed using thermophilic ligand-binding moieties, including protein ligand-binding moieties from hyperthermophilic and thermophilic organisms. One embodiment, among others, is an isolated nucleic acid which encodes a maltose/maltodextrin-binding fluorescent indicator, the indicator comprising: a maltose/maltodextrin-binding protein moiety from a hyperthermophilic or thermophilic organism, a donor fluorophore moiety covalently coupled to the maltose/maltodextrin-binding protein moiety, and an acceptor fluorophore moiety covalently coupled to the maltose/maltodextrin-binding protein moiety, wherein FRET between the donor moiety and the acceptor moiety is altered when the donor moiety is excited and maltose or maltodextrin binds to the maltose/maltodextrin-binding protein moiety. Preferred maltose/maltodextrin-binding protein moieties are maltose/maltodextrin binding protein moieties from the hyperthermophile *Pyrococcus furiosus* and thermo-acidophile *Alicyclobacillus acidocaldarius*.

As used herein, "covalently coupled" means that the donor and acceptor fluorescent moieties may be conjugated to the ligand binding protein moiety via a chemical linkage, for instance to a selected amino acid in said ligand-binding protein moiety. Covalently coupled also means that the donor and acceptor moieties may be genetically fused to the ligand binding protein moiety such that the ligand binding protein moiety is expressed as a fusion protein comprising the donor and acceptor moieties.

Either the donor fluorophore moiety or the acceptor fluorophore moiety or both may be fused to an internal site of said ligand binding protein moiety. Preferably, the donor and acceptor moieties are not fused in tandem, although the donor and acceptor moieties may be contained on the same protein domain or lobe. A domain is a portion of a protein that performs a particular function and is typically at least about 40 to about 50 amino acids in length. There may be several protein domains contained in a single protein. A "ligand binding protein moiety" according to the present invention can be a complete, naturally occurring protein sequence, or at least the ligand binding portion or portions thereof. In preferred embodiments, among others, a ligand binding moiety of the invention is at least about 40 to about 50 amino acids in length, or at least about 50 to about 100 amino acids in length, or more than about 100 amino acids in length.

A preferred ligand-binding protein moiety, among others, is a maltose/maltodextrin-binding protein moiety from *Pyrococcus furiosus* (ATCC 43587) malE protein. The DNA sequence of *Pyrococcus* malE (SEQ ID No. 1) and its protein sequence (SEQ ID No. 2) are known in the art. Another preferred ligand-binding protein moiety, is a maltose/maltodextrin-binding protein moiety from *Alicyclobacillus acidocaldarius* malE protein. The DNA sequence of *Alicyclobacillus* malE (SEQ ID No. 3) and its protein sequence (SEQ ID No. 4) are also known in the art. Any portion of the malE DNA sequence which encodes a maltose/maltodextrin-binding region may be used in the nucleic acids of the present invention. Maltose/maltodextrin-binding portions of malE or any of its homologues from other thermophilic and hyperthermophilic organisms may be cloned into the vectors described herein and screened for activity according to the disclosed assays.

Naturally occurring species variants of malE may also be used, in addition to artificially engineered variants comprising site-specific mutations, deletions or insertions that maintain measurable maltose/maltodextrin-binding function, as well as derivatives which are intentionally engineered to bind to another small molecule, either similar to maltose or maltodextrin in size and chemical composition, e.g. sucrose, or different, e.g. auxin or serotonin. Variant nucleic acid sequences suitable for use in the nucleic acid constructs of the present invention will preferably have at least 70, 75, 80, 85, 90, 95, or 99% similarity or identity to the gene sequence for malE. Suitable variant nucleic acid sequences may also hybridize to the gene for malE under highly stringent hybridization conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993), which is herein incorporated by reference. Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

Preferred artificial variants of the present invention may be designed to exhibit decreased affinity for the ligand, in order to expand the range of ligand concentration that can be measured by the disclosed nanosensors. Additional artificial variants showing decreased or increased binding affinity for ligands may be constructed by random or site-directed mutagenesis and other known mutagenesis techniques, and cloned into the vectors described herein and screened for activity according to the disclosed assays. The binding specificity of disclosed biosensors may be also be altered by mutagenesis so as to alter the ligand recognized by the biosensor. See, for instance, Looger et al., Nature, 423 (6936): 185-190.

The sensors of the invention may also be designed with a reporter element different from a donor/acceptor pair of FRET-compatible fluorescent proteins. For instance, the ligand-binding moiety of the sensor may be fused with an enzyme in such a manner to create an allosterically regulated enzyme whose activity is regulated by a specified ligand (Guntas and Ostermeier, 2004, J. Mol. Biol. 336 (1): 263-73). In addition, such an allosterically-regulated reporter domain may be divided into two or more separate and complementing halves, e.g. complementing fragments of β-lactamase (Galarneau et al., 2002, Nature Biotechnol. 20: 619-622) or of GFP (Cabantous et al., 2005, Nature Biotechnol. 23: 102-107). Any and all reporter element fragments may be fused with the ligand-binding moiety in either an end-to-end fashion (e.g. a typical fusion protein) or inserted internally into the sequence of the ligand-binding moiety (e.g. a loop-inserted fluorescent protein as described herein).

The isolated nucleic acids of the invention may incorporate any suitable donor and acceptor fluorophore moieties that are capable in combination of serving as donor and acceptor moieties in FRET. Preferred donor and acceptor moieties are selected from the group consisting of GFP (green fluorescent protein), CFP (cyan fluorescent protein), BFP (blue fluorescent protein), YFP (yellow fluorescent protein), and enhanced variants thereof, with a particularly preferred embodiment provided by the pair of CFP donor/YFP-Venus, a variant of YFP with improved pH tolerance and maturation time (Nagai, T., Ibata, K., Park, E. S., Kubota, M., Mikoshiba, K., and Miyawaki, A. (2002) A variant of yellow fluorescent protein with fast and efficient maturation for cell-biological applications. Nat. Biotechnol. 20, 87-90), acceptor. An alternative is the MiCy/mKO pair with higher pH stability and a larger spectral separation (Karasawa S, Araki T, Nagai T, Mizuno H, Miyawaki A. Cyan-emitting and orange-emitting fluorescent proteins as a donor/acceptor pair for fluorescence resonance energy transfer. Biochem J. 2004 381:307-12). Also suitable as either a donor or acceptor is native DsRed from a Discosoma species, an ortholog of DsRed from another genus, or a variant of a native DsRed with optimized properties (e.g. a K83M variant or DsRed2 (available from Clontech)). Criteria to consider when selecting donor and acceptor fluorescent moieties is known in the art, for instance as disclosed in U.S. Pat. No. 6,197,928, which is herein incorporated by reference in its entirety.

When the fluorophores of the biosensor contain stretches of similar or related sequence(s), the present inventors have recently discovered that gene silencing may adversely affect expression of the biosensor in certain cells and particularly whole organisms. In such instances, it is possible to modify the fluorophore coding sequences at one or more degenerate or wobble positions of the codons of each fluorophore, such that the nucleic acid sequences of the fluorophores are modified but not the encoded amino acid sequences. Alternative, one or more conservative substitutions that do not adversely affect the function of the fluorophores may also be incorporated. See PCT application PCT/US2005/036953, "Methods of Reducing Repeat-Induced Silencing of Transgene Expression and Improved Fluorescent Biosensors, which is herein incorporated by reference in its entirety.

As used herein, the term "variant" is intended to refer to polypeptides with at least about 70%, more preferably at least 75% identity, including at least 80%, 90%, 95% or greater identity to native fluorescent molecules. Many such variants are known in the art, or can be readily prepared by random or directed mutagenesis of a native fluorescent molecules (see, for example, Fradkov et al., FEBS Lett. 479:127-130 (2000)). It is also possible to use dyes, alone or in combination with the fluorophores listed above, including but not limited to TOTO dyes (Laib and Seeger, 2004, J Fluoresc. 14 (2):187-91), Cy3 and Cy5 (Churchman et al., 2005, Proc Natl Acad Sci U S A. 102 (5): 1419-23), Texas Red, fluorescein, and tetramethylrhodamine (TAMRA) (Unruh et al., Photochem Photobiol. 2004 Oct. 1), AlexaFluor 488, to name a few, as well as fluorescent tags (see, for example, Hoffman et al., 2005, Nat. Methods 2 (3): 171-76).

It is also possible to use luminescent quantum dots (QD) or pebble-coupled approaches for FRET (Clapp et al., 2005, J.

Am. Chem. Soc. 127 (4): 1242-50; Medintz et al., 2004, Proc. Natl. Acad. Sci. USA 101 (26): 9612-17; Buck et al., 2004, Curr. Opin. Chem. Biol. 8 (5): 540-6), including Surface-Enhanced Raman Scattering, where sensors are bound to the surface of nanoparticles and detection is achieved by Raman spectroscopy (Haes and Van Duyne, 2004, Expert Rev. Mol. Diagn. 4 (4): 527-37).

Bioluminescence resonance energy transfer (BRET) may also be used for both in vitro and in vivo measurements, and offers the advantages of FRET without the consequences of fluorescence excitation. BRET is a naturally occurring phenomenon. For instance, when the photoprotein aequorin is purified from the jellyfish, *Aequorea*, it emits blue light in the absence of GFP, but when GFP and aequorin are associated as they are in vivo, GFP accepts the energy from aequorin and emits green light. In BRET, the donor fluorophore of the FRET technique is replaced by a luciferase. In the presence of a substrate, bioluminescence from the luciferase excites the acceptor fluorophore through the same Forster resonance energy transfer mechanisms described above. Thus, by using a luciferase/GFP mutant or other fluorophore combination, BRET can be used to measure protein interactions both in vivo and in vitro (see Xu et al, 1999, Proc. Natl. Acad. Sci. USA 96: 151-56, which is herein incorporated by reference).

The invention further provides vectors containing isolated nucleic acid molecules encoding the biosensor polypeptides described herein. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. Such vectors include expression vectors containing expression control sequences operatively linked to the nucleic acid sequence coding for the biosensor. Vectors may be adapted for function in a prokaryotic cell, such as *E. coli* or other bacteria, or a eukaryotic cell, including yeast and animal cells. For instance, the vectors of the invention will generally contain elements such as an origin of replication compatible with the intended host cells, one or more selectable markers compatible with the intended host cells and one or more multiple cloning sites. The choice of particular elements to include in a vector will depend on factors such as the intended host cells, the insert size, whether regulated expression of the inserted sequence is desired, for instance through the use of an inducible or regulatable promoter, the desired copy number of the vector, the desired selection system, and the like. The factors involved in ensuring compatibility between a host cell and a vector for different applications are well known in the art.

Preferred vectors for use in the present invention will permit cloning of the ligand binding domain or receptor between nucleic acids encoding donor and acceptor fluorescent molecules, resulting in expression of a chimeric or fusion protein comprising the ligand binding domain covalently coupled to donor and acceptor fluorescent molecules. Exemplary vectors include the bacterial pRSET-FLIP derivatives disclosed in Fehr et al. (2002) (Visualization of maltose uptake in living yeast cells by fluorescent nanosensors. Proc. Natl. Acad. Sci. U S A 99, 9846-9851), which is herein incorporated by reference in its entirety. Methods of cloning nucleic acids into vectors in the correct frame so as to express a fusion protein are well known in the art.

The chimeric nucleic acids of the present invention are preferably constructed such that the donor and acceptor fluorescent moiety coding sequences are fused to separate termini of the ligand binding domain in a manner such that changes in FRET between donor and acceptor may be detected upon ligand binding. Fluorescent domains can optionally be separated from the ligand binding domain by one or more flexible linker sequences. Such linker moieties are preferably between about 1 and 50 amino acid residues in length, and more preferably between about 1 and 30 amino acid residues. Linker moieties and their applications are well known in the art and described, for example, in U.S. Pat. Nos. 5,998,204 and 5,981,200, and Newton et al., Biochemistry 35:545-553 (1996). Alternatively, shortened versions of any of the fluorophores described herein may be used.

It will also be possible depending on the nature and size of the ligand-binding domain to insert one or both of the fluorescent molecule coding sequences within the open reading frame of the ligand-binding protein such that the fluorescent moieties are expressed and displayed from a location within the biosensor rather than at the termini. Such sensors are generally described in U.S. application Ser. No. 11/665,339, which is herein incorporated by reference in its entirety. It will also be possible to insert a ligand binding sequence, such as a sequence encoding malE or other maltose/maltodextrin binding domain, into a single fluorophore coding sequence, i.e. a sequence encoding a GFP, YFP, CFP, BFP, etc., rather than between tandem molecules. According to the disclosures of U.S. Pat. Nos. 6,469,154 and 6,783,958, each of which is incorporated herein by reference in their entirety, such sensors respond by producing detectable changes within the protein that influence the activity of the fluorophore.

The invention also includes host cells transfected with a vector or an expression vector of the invention, including prokaryotic cells, such as *E. coli* or other bacteria, or eukaryotic cells, such as yeast cells or animal cells. In another aspect, the invention features a transgenic non-human animal having a phenotype characterized by expression of the nucleic acid sequence coding for the expression of the environmentally stable biosensor. The phenotype is conferred by a transgene contained in the somatic and germ cells of the animal, which may be produced by (a) introducing a transgene into a zygote of an animal, the transgene comprising a DNA construct encoding the environmentally stable biosensor; (b) transplanting the zygote into a pseudopregnant animal; (c) allowing the zygote to develop to term; and (d) identifying at least one transgenic offspring containing the transgene. The step of introducing of the transgene into the embryo can be by introducing an embryonic stem cell containing the transgene into the embryo, or infecting the embryo with a retrovirus containing the transgene. Transgenic animals of the invention include transgenic *C. elegans* and transgenic mice and other animals.

The present invention also encompasses isolated environmentally stable biosensor molecules having the properties described herein, particularly binding fluorescent indicators constructed using hyperthermophilic and moderately thermophilic proteins. Such polypeptides may be recombinantly expressed using the nucleic acid constructs described herein, or produced by chemically coupling some or all of the component domains. The expressed polypeptides can optionally be produced in and/or isolated from a transcription-translation system or from a recombinant cell, by biochemical and/or immunological purification methods known in the art. The polypeptides of the invention can be introduced into a lipid bilayer, such as a cellular membrane extract, or an artificial lipid bilayer (e.g. a liposome vesicle) or nanoparticle.

Methods of Detecting Analytes

The nucleic acids and proteins of the present invention are useful for detecting ligand binding and measuring changes in the levels of analytes both in vitro and in an animal. In one embodiment, the invention comprises a method of detecting changes in the level of an analyte in a sample of cells, comprising (a) providing a cell expressing a nucleic acid encoding an environmentally biosensor as described herein and a sample of cells; and (b) detecting a change in FRET between a donor fluorophore moiety and an acceptor fluorophore moiety, each covalently attached to the ligand or analyte binding domain, wherein a change in FRET between said donor moiety and said acceptor moiety indicates a change in the level of analyte in the sample of cells.

FRET may be measured using a variety of techniques known in the art. For instance, the step of determining FRET may comprise measuring light emitted from the acceptor fluorophore moiety. Alternatively, the step of determining FRET may comprise measuring light emitted from the donor fluorophore moiety, measuring light emitted from the acceptor fluorophore moiety, and calculating a ratio of the light emitted from the donor fluorophore moiety and the light emitted from the acceptor fluorophore moiety. The step of determining FRET may also comprise measuring the excited state lifetime of the donor moiety or anisotropy changes (Squire A, Verveer P J, Rocks O, Bastiaens P I. J. Struct Biol. 2004 147 (1):62-9. Red-edge anisotropy microscopy enables dynamic imaging of homo-FRET between green fluorescent proteins in cells.). Such methods are known in the art and described generally in U.S. Pat. No. 6,197,928, which is herein incorporated by reference in its entirety.

The amount of ligand or analyte in a sample of cells can be determined by determining the degree of FRET. First the sensor must be introduced into the sample. Changes in analyte concentration can be determined by monitoring FRET at a first and second time after contact between the sample and the fluorescent indicator and determining the difference in the degree of FRET. The amount of analyte in the sample can be quantified for example by using a calibration curve established by titration.

The cell sample to be analyzed by the methods of the invention may be contained in vivo, for instance in the measurement of ligand transport on the surface of cells, or in vitro, wherein ligand efflux may be measured in cell culture. Alternatively, a fluid extract from cells or tissues may be used as a sample from which ligands are detected or measured.

Methods for detecting analyte levels as disclosed herein may be used to screen and identify compounds that may be used to modulate analyte concentrations and ligand binding. In one embodiment, among others, the invention comprises a method of identifying a compound that modulates ligand binding comprising (a) contacting a mixture comprising a cell expressing an environmentally stable biosensor as disclosed herein and a sample of cells with one or more test compounds, and (b) determining FRET between said donor fluorescent domain and said acceptor fluorescent domain following said contacting, wherein increased or decreased FRET following said contacting indicates that said test compound is a compound that modulates ligand binding activity.

The term "modulate" in this embodiment means that such compounds may increase or decrease ligand binding activity. Compounds that increase ligand binding activity may be targets for therapeutic intervention and treatment of disorders associated with aberrant ligand activity, as described above. Compounds that decrease ligand binding activity may be developed into therapeutic products for the treatment of disorders associated with ligand binding activity.

The methods of the present invention may also be used as a tool for high throughput and high content drug screening. For instance, a solid support or multiwell dish comprising the biosensors of the present invention may be used to screen multiple potential drug candidates simultaneously. Thus, the invention comprises a high throughput method of identifying compounds that modulate binding of a ligand to a receptor, comprising (a) contacting a solid support comprising at least one biosensor of the present invention, or at least one cell expressing a biosensor nucleic acid of the present invention, with said ligand and a plurality of test compounds; and (b) determining FRET between said donor fluorescent domain and said acceptor fluorescent domain following said contacting, wherein increased or decreased FRET following said contacting indicates that a particular test compound is a compound that modulates ligand binding.

The targeting of the sensor to the outer leaflet of the plasma membrane is only one embodiment of the potential applications. It demonstrates that the nanosensor can be targeted to a specific compartment. Alternatively, other targeting sequences may be used to express the sensors in other compartments such as vesicles, ER, vacuole, etc.

The following examples are provided to describe and illustrate the present invention. As such, they should not be construed to limit the scope of the invention. Those in the art will well appreciate that many other embodiments also fall within the scope of the invention, as it is described hereinabove and in the claims.

EXAMPLES

Example 1

Sensor Construction

Initially, the thermophilic-derived nanosensor construct was obtained from *Pyrococcus furiosus*, e.g., the maltose-binding protein (malE) sensor (malE_Pf). Several more thermophilic-derived sensors have been constructed (malE from *Thermococcus litoralis*, malE from *Thermus thermophilus* (malE_Tt), mglB from *Thermus thermophilus*, q72hc2 (a branched amino-acid binding protein) from *Thermus thermophilus*, 2609 (an amino-acid binding protein) from *Thermus thermophilus*, 1033 (a glutamate-binding protein) from *Thermus thermophilus*, and malE from *Alicyclobacillus acidocaldarius* (malE_Aa)).

The maltose-binding protein (malE) from *Alicyclobacillus acidocaldarius* was chosen as a high-priority target for nanosensor construction because of its known thermal stability and acid resistance. The malE gene was isolated from genomic DNA by PCR and moved into the FLIP format using the recently-developed GATEWAY_FLIP cloning strategy. The same method applies to the construction of the malE_Pf nanosensor.

Figure 1B:
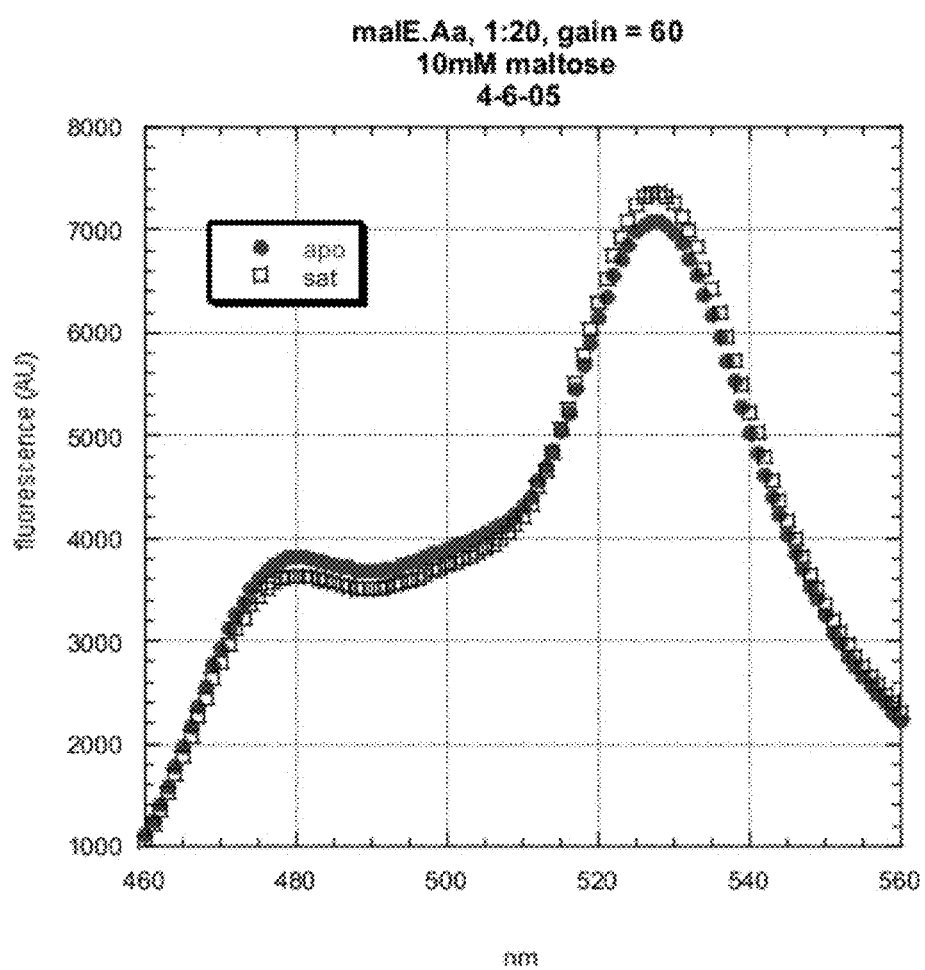

FIG. 1a shows substrate-induced FRET changes in the malE-Pf sensor. FIG. 1b shows substrate-induced FRET changes in the malE_Aa sensor. The Figures indicate that the spectra in the presence and absences of 10 mM maltose have an isobestic point at around 510 nm for both the malE_Pf and malE_Aa sensors. Spectra were obtained in 10 mM TRIS buffer, pH 7.9, with protein concentration approximately 100 nM. Excitation filter was 433/−12 nm, emission filters for CFP and YFP emission were 481/−12 and 526/−12 nm, respectively.

Figure 2A:
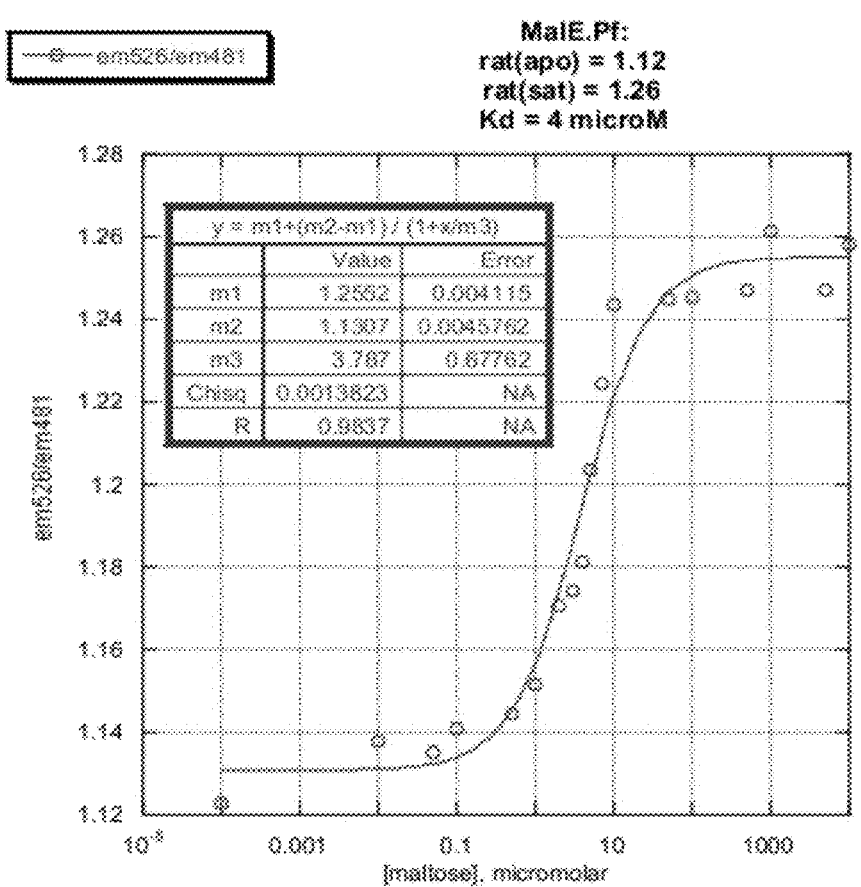
FIGS. 2a and 2b, depicts titration curves for malE_Pf and malE_Aa nanosensors.
Figure 2B:
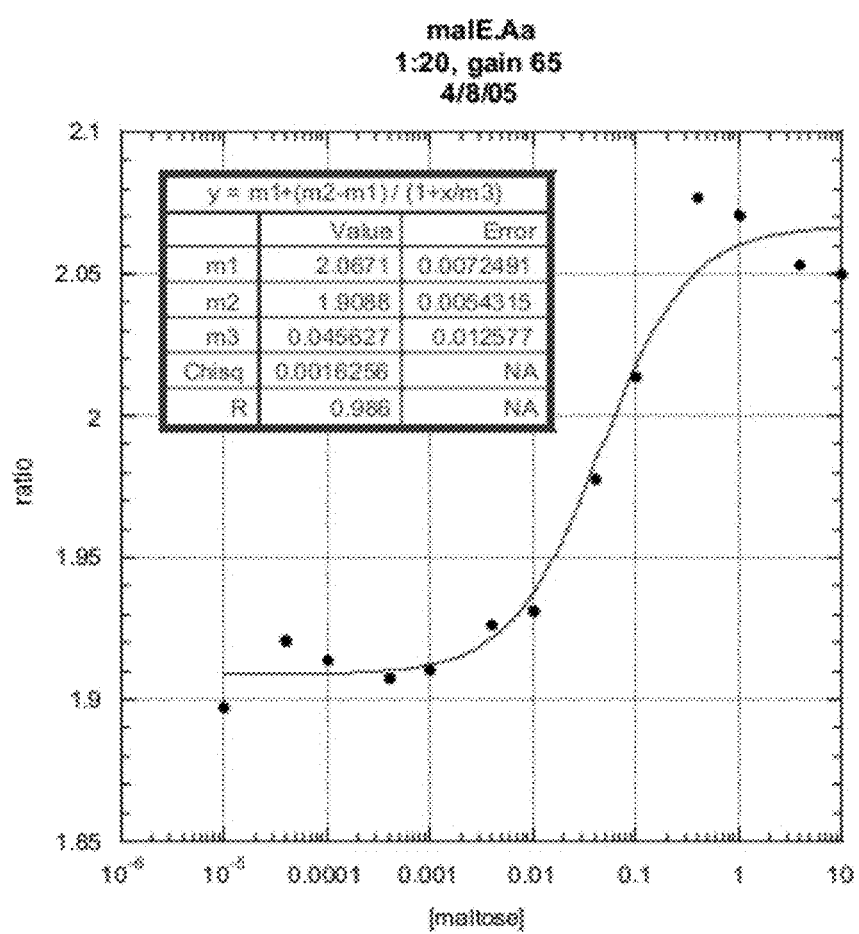
Figure 3A:
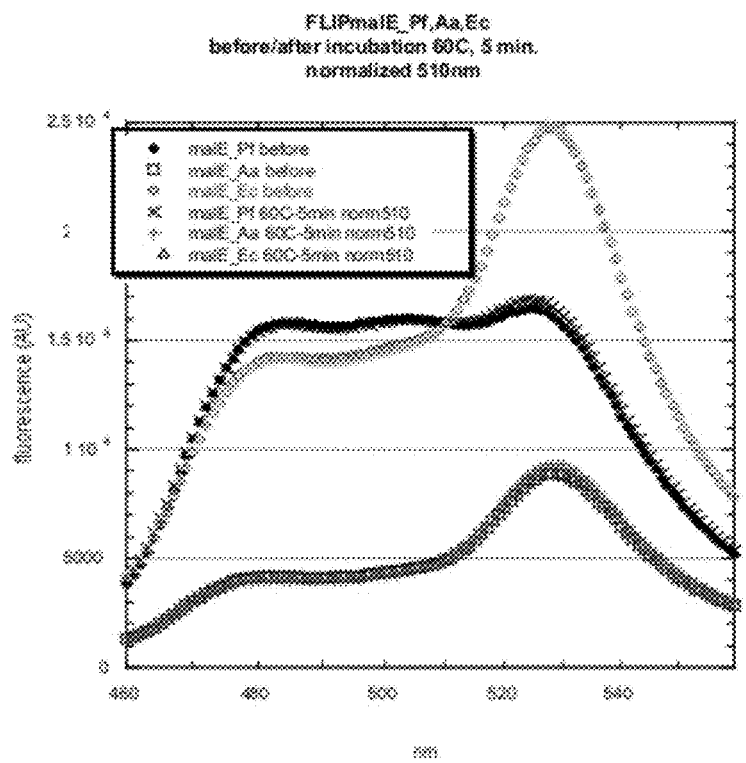
(FIGS. 3a and 3b), 75° C.
Figure 3B:
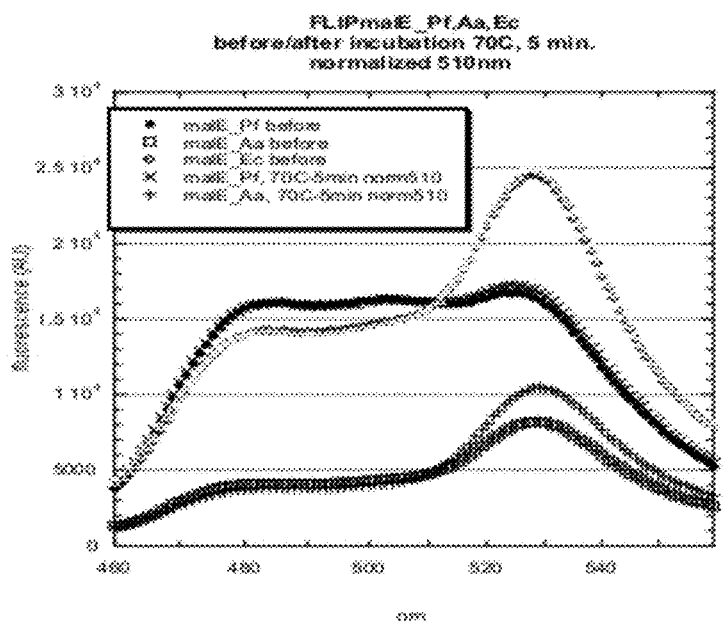
Figure 3C:
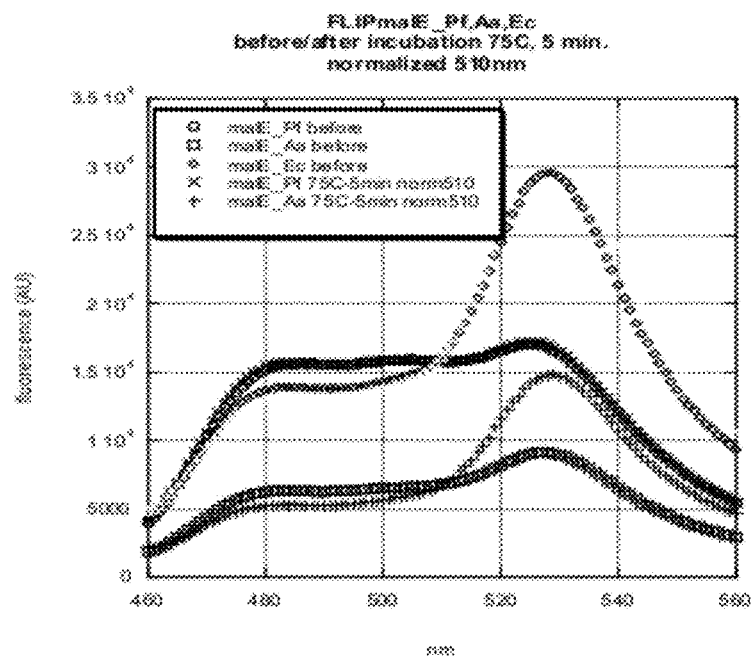
(FIG. 3c) 80° C.
Figure 3D:
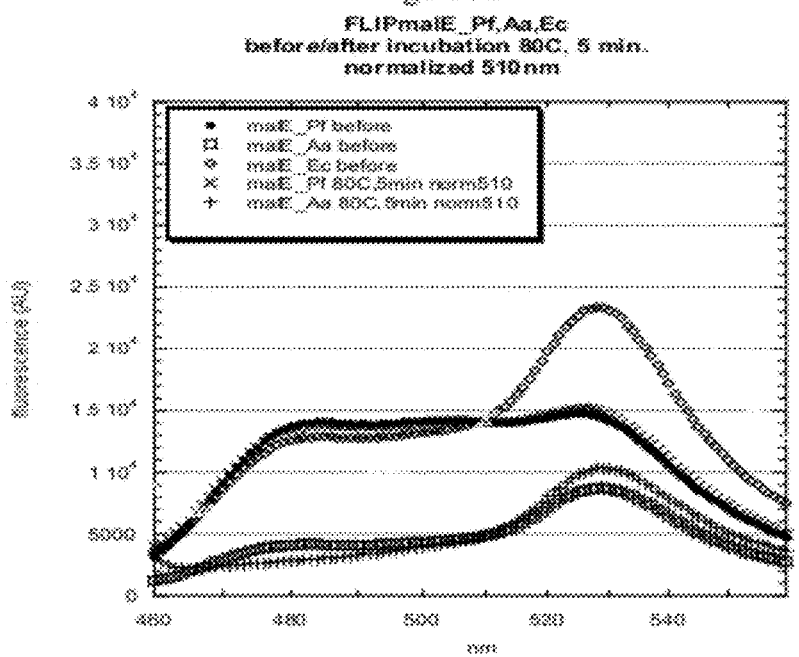
(FIG. 3d), 85° C.
Figure 4A:
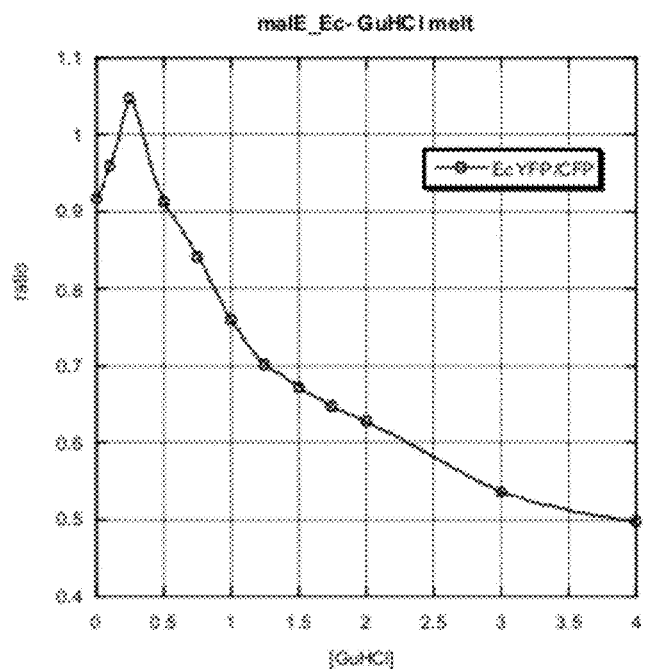
FIG. 4 compares the resistance of malE_Pf, MalE_Aa, and MalE_Ec nanosensors to guanidinium hydrochloride (Gu-HCL) denaturation at varying GuHCl pH (FIGS. 4a-4c), and at pH 4.1 (FIGS. 4d-4f).
Figure 4B:
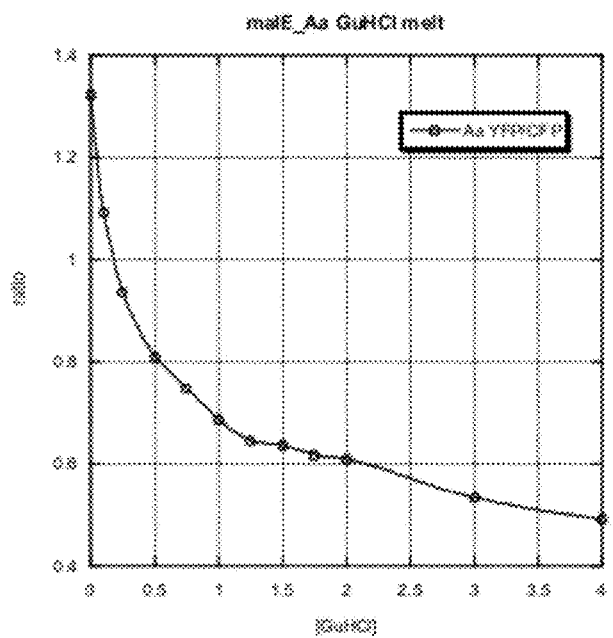
Figure 4C:
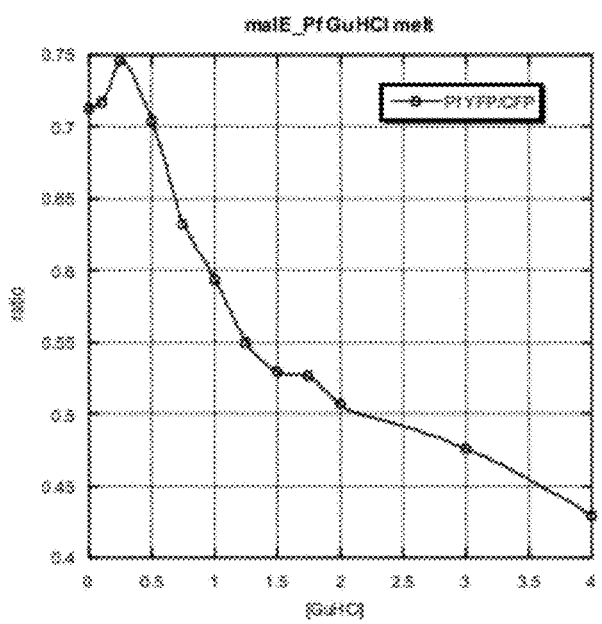
Figure 4D:
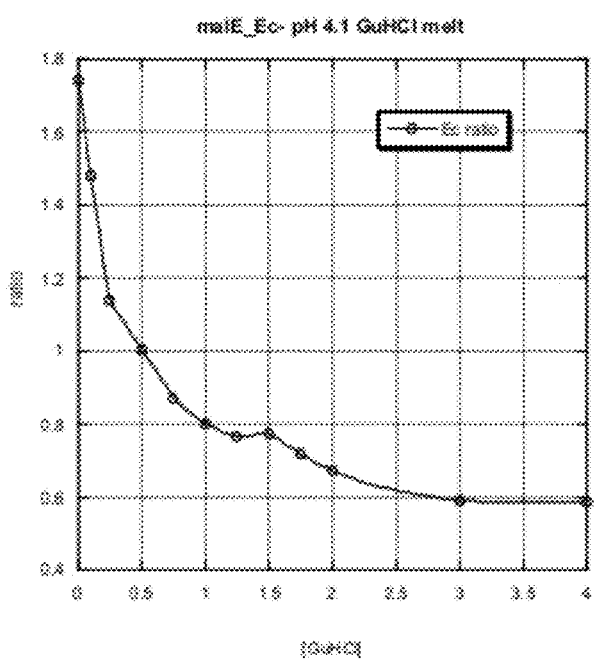
Figure 4E:
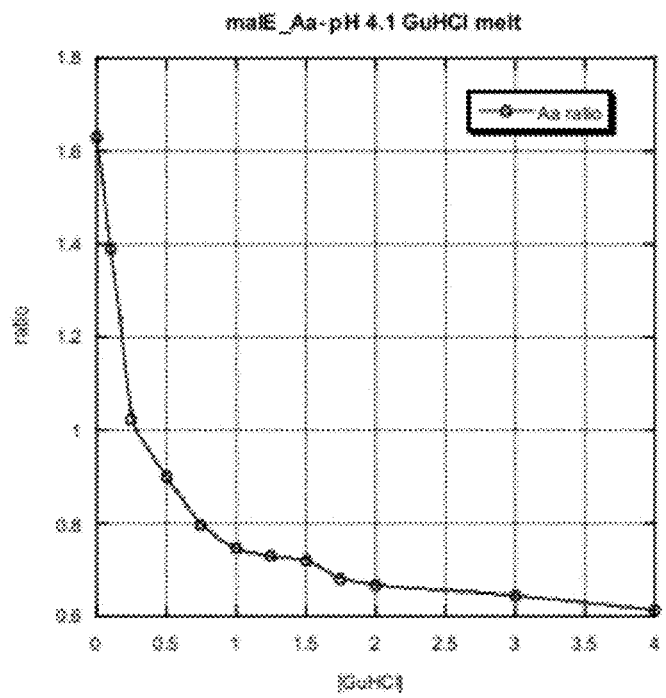
Figure 4F:
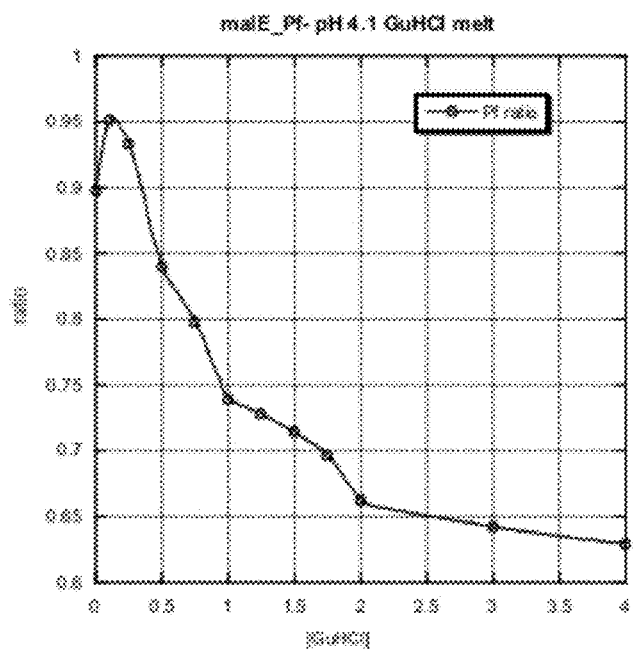

In FIGS. 2a and 2b, the in vitro substrate titration curves for malE_Pf and malE_Aa nanosensors were obtained by calculating the maltose-dependent ratio change. Addition of maltose resulted in a decrease in CFP emission and an increase in YFP emission (a net effect of increase in the YFP/CFP ratio). By nonlinear regression, the $K_d$ of malE_Pf was determined to be 4 µM. Emission spectra and substrate titration curves were obtained by using monochromator microplate reader Safire (Tecan, Austria). The excitation filter was 433/−12 nm, emission filters for CFP and YFP emission were 481/−12 and 526/−12 nm, respectively. All analyses were done in 10 mM TRIS buffer, pH 7.9, with protein concentration approximately 100 nM.

The genetically-encoded FLIP sensor format is readily accessible to assays and screens of sensor stability and response in a variety of environmental conditions. The extreme stability of the fluorescent protein (FP) groups in the FLIP ensures that in the presence of a stable binding protein (BP), the FLIP sensor will be robust. We have assayed the stability of the malE_Pf and malE_Aa (and for a control comparison, the malE_Ec sensors from *E. coli*) against three forms of denaturation: thermal, chemical (guanidinium hydrochloride), and acid.

Example 2

Temperature Resistance

The three nanosensors were exposed to elevated temperatures (from 60° C. to 95° C.) for five minutes, then brought back down to room temperature and promptly analyzed in the fluorimeter. All sensors showed no adverse effects from exposure to 60° C. The mal_Aa protein showed some sensitivity to exposure to 70° C., and was destabilized by 85° C. The malE_Ec nanosensor showed slightly less sensitivity to 70° C., but was destabilized soon thereafter. The malE_Pf sensor showed no sensitivity to temperatures up to 80° C., and it is likely that the FPs unfold at ~85° C., leading to the collapse of the signal of all three sensors in this region (FIG. 3). The increase of the fluorescence signal upon partial destabilization has been seen before, and is likely due to formation of a molten globule state.

Example 3

Chemical Denaturant Resistance

The three sensors were also exposed to increasing concentrations of the chemical denaturant GuHCl (guanidinium hydrochloride), and fluorescence spectra were recorded. Again, the extreme conditions affect both the BP and FP portions of the nanosensors, and as well the high chloride concentration in the GuHCl solutions leads to some quenching of the FPs, particularly the YFP. In spite of this, it is possible to observe trends between the different sensors. The malE_Pf sensor is by far the most resistant to GuHCl denaturation, at neutral pH. After this, the malE_Ec and then lastly the malE_Aa sensor follow. Upon exposure to low pH (4.1), the malE_Pf sensor is still the most stable, but has been destabilized. The malE_Aa sensor follows this, somewhat destabilized versus neutral pH. The malE_Ec has been significantly destabilized by exposure to very acid pH (FIG. 4).

Example 4 pH Resistance of FLIP-malE Nanosensors

Figure 5:
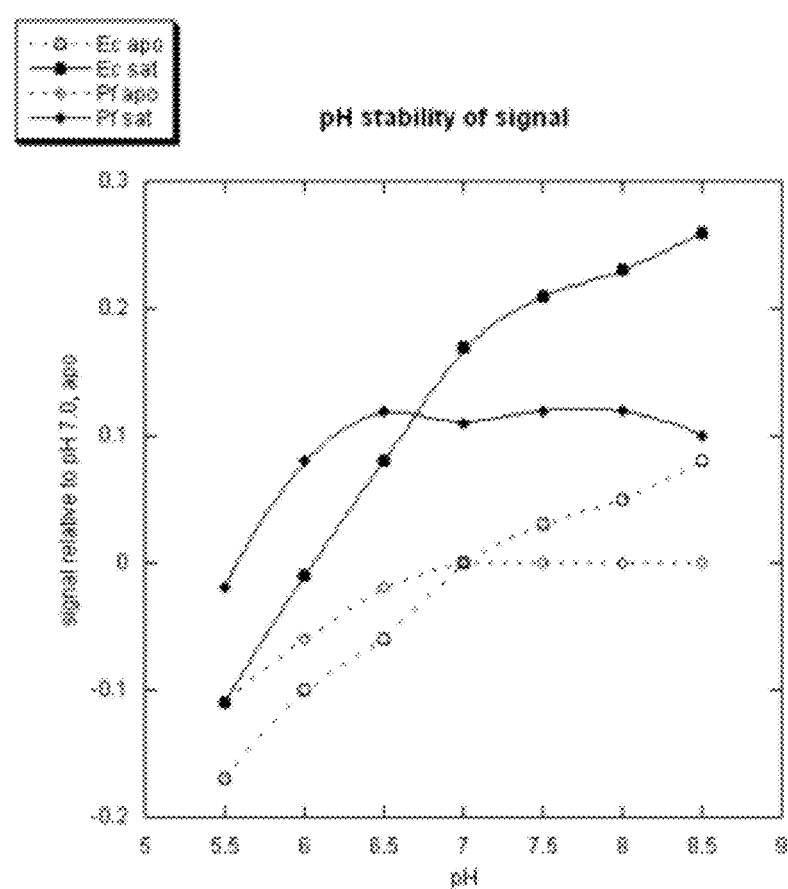
FIG. 5 shows pH stability of the hyperthermophilic FLIP-malE_Pf and the mesophilic FLIP-malE_Ec nanosensors.
Figure 6A:
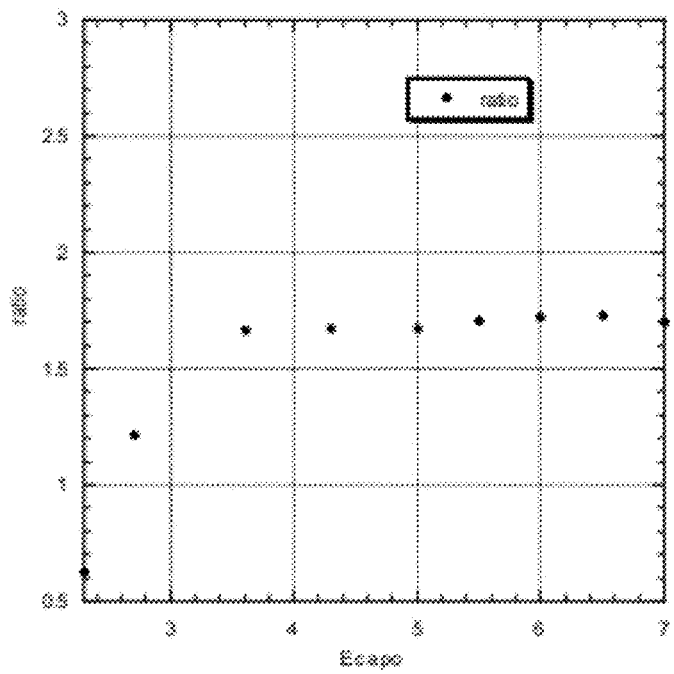
FIG. 6 shows stability of fluorescence signal of malE_Pf (FIGS. 6a and 6b), malE_Aa (FIGS. 6c and 6d) and malE_Ec (FIGS. 6e and 6f) nanosensors at variant pH.
Figure 6B:
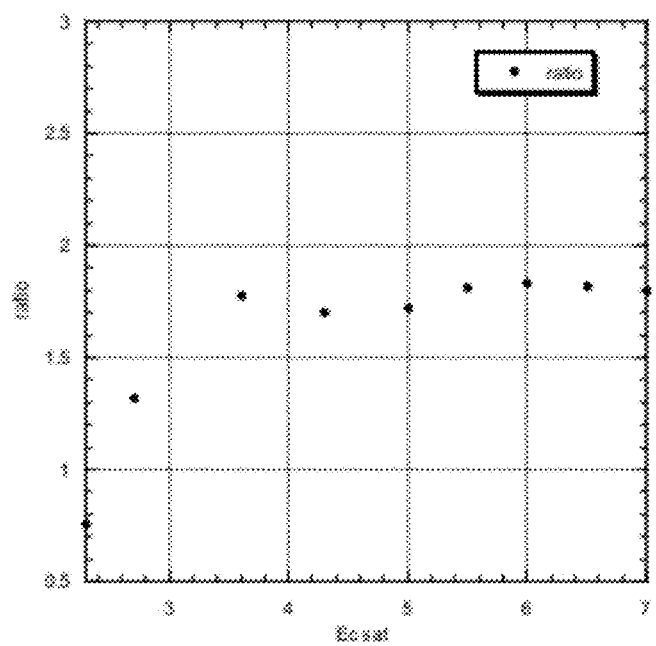
Figure 6C:
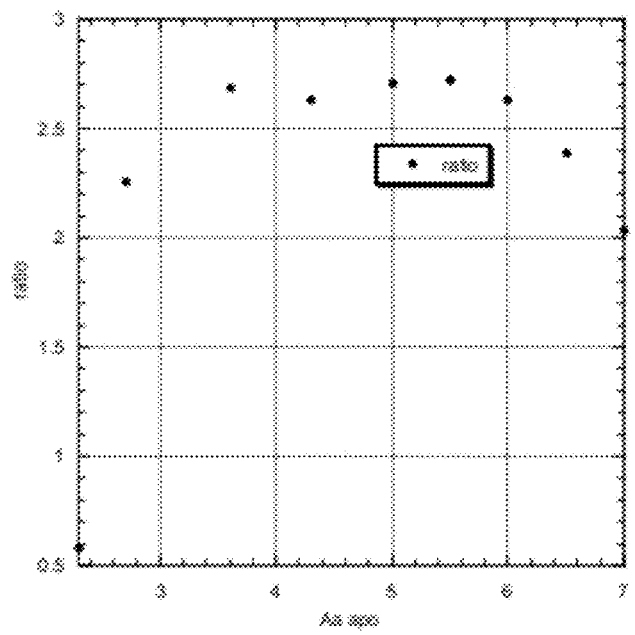
Figure 6D:
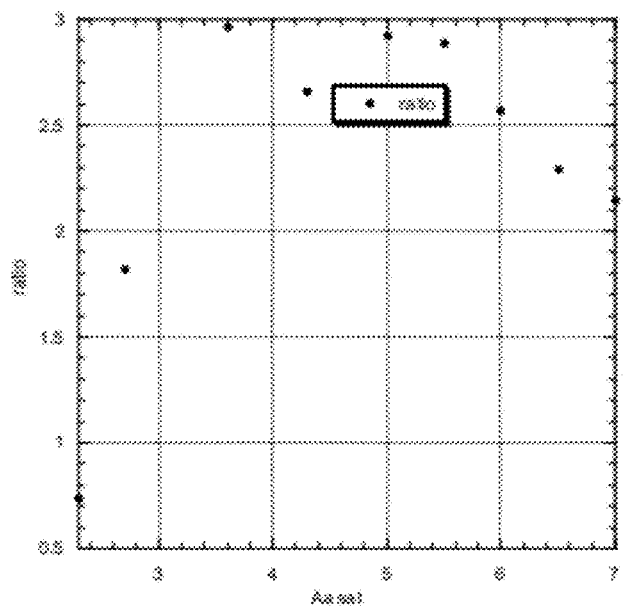
Figure 6E:
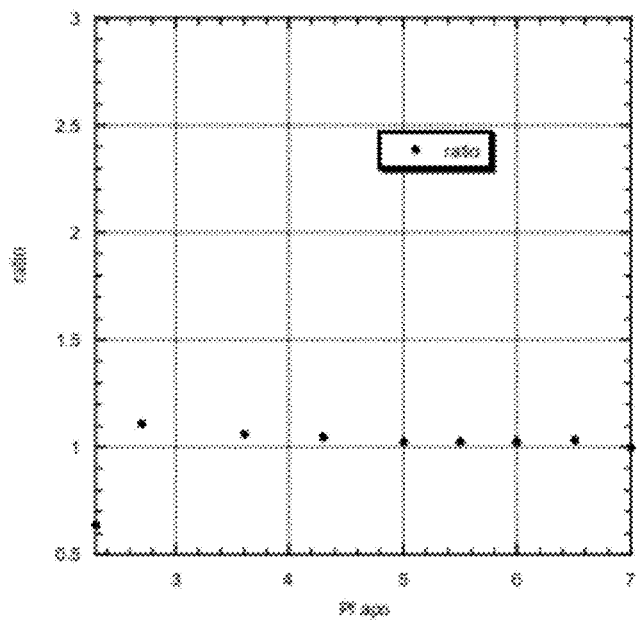
Figure 6F:
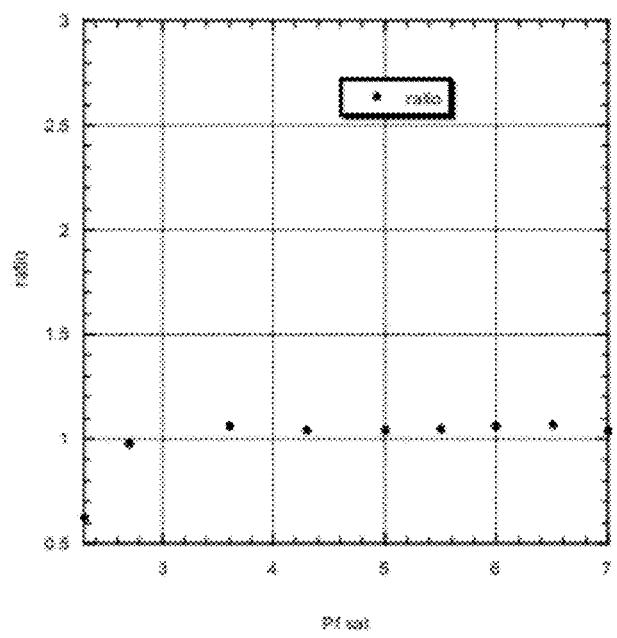

FIG. 5 is a comparison of the stability of the hyperthermophilic FLIP-malE_Pf nanosensors and mesophilic FLIP-malE_Ec nanosensors at different pH values. Experiments were performed in 20 mM phosphate buffer, pH 5.5 to 8.5. The FLIP-malE_Pf sensor is shown to be more tolerant to pH changes, with much smaller signal fluctuations than the FLIP-malE_Ec sensor.

Example 5

Stability of Fluorescence Signal at Variant pH

In addition to being stable in extreme conditions, the nanosensors should retain normal functionality, particularly if it is difficult to calibrate them in this novel environment (e.g., the inside of a cell). The three nanosensors were exposed to a range of pH from 2.3 to 7.0, and fluorescence signal was measured in the absence and presence of saturating ligand (100 µM maltose), in 20 mM MOPS buffer. The malE_Pf sensor was completely resistant to pH effects down to pH 2.7, with only slight effects at pH 2.3. The malE_Ec sensor was sensitive below pH 3.5. The malE_Aa sensor, despite being the most resistant to acid-destabilization, is most affected by pH changes, and thus will require further engineering before functioning as a reliable maltose sensor at extremely low pH (FIG. 6).

All publications, patents and patent applications discussed herein are incorporated herein by reference. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. An isolated nucleic acid encoding a maltose binding sensor, the nucleic acid comprising:
   the polynucleotide sequence of SEQ ID NO:1 or SEQ ID NO:3;
   a polynucleotide sequence encoding a donor fluorophore moiety; and
   a polynucleotide sequence encoding an acceptor fluorophore moiety.

2. The isolated nucleic acid of claim 1, wherein the polynucleotide sequence encoding the donor fluorophore moiety encodes a moiety selected from the group consisting of a green fluorescent protein (GFP), a cyan fluorescent protein (CFP), a blue fluorescent protein (BFP), a yellow fluorescent protein (YFP), a dsRED fluorescent protein, CoralHue Midoriishi-Cyan (MiCy) and monomeric CoralHue Kusabira-Orange (mKO).

3. The isolated nucleic acid of claim 1, wherein the polynucleotide sequence encoding the acceptor fluorophore moiety encodes a moiety selected from the group consisting of green fluorescent protein (GFP), a cyan fluorescent protein (CFP), a blue fluorescent protein (BFP), a yellow fluorescent protein (YFP), a dsRED fluorescent protein, CoralHue Midoriishi-Cyan (MiCy) and monomeric CoralHue Kusabira-Orange (mKO).

4. The isolated nucleic acid of claim 1, wherein the polynucleotide sequence encoding the donor fluorophore moiety encodes CFP and the polynucleotide sequence encoding the acceptor fluorophore moiety encodes YFP Venus.

5. The isolated nucleic acid of claim 1, further comprising a polynucleotide that encodes at least one linker moiety.

6. An isolated cell comprising the nucleic acid of claim 1.

7. An isolated expression vector comprising the nucleic acid of claim 1.

8. The expression vector of claim 7 adapted for function in a prokaryotic cell.

9. The expression vector of claim 7 adapted for function in a eukaryotic cell.

10. An isolated cell comprising the vector of claim 7.

11. The cell of claim 10, wherein the cell is a prokaryote.

12. The cell of claim 10, wherein the cell is a eukaryotic cell.

13. The cell of claim 12, wherein the cell is a yeast cell.

14. The cell of claim 12, wherein the cell is an animal cell.

15. A method of detecting changes in the level of ligand in a sample of cells, comprising:
   (a) providing a cell expressing the nucleic acid of claim 1; and
   (b) detecting a change in FRET between said donor fluorophore moiety and said acceptor fluorophore moiety,
   wherein a change in FRET between said donor moiety and said acceptor moiety indicates a change in the level of ligand in a sample of cells.

16. The method of claim 15, wherein the step of determining FRET comprises measuring light emitted from the acceptor fluorophore moiety.

17. The method of claim 15, wherein determining FRET comprises measuring light emitted from the donor fluorophore moiety, measuring light emitted from the acceptor fluorophore moiety, and calculating a ratio of the light emitted from the donor fluorophore moiety and the light emitted from the acceptor fluorophore moiety.

18. The method of claim 15, wherein the step of determining FRET comprises measuring the excited state lifetime of the donor moiety.

19. The method of claim 15, wherein said sample of cells is contained in vitro.

20. A method of identifying a compound that modulates the binding of a ligand to its receptor, comprising:
   (a) contacting a cell expressing the nucleic acid of claim 1 with one or more test compounds in the presence of said ligand; and
   (b) determining FRET between said donor fluorescent domain and said acceptor fluorescent domain following said contacting,
   wherein increased or decreased FRET following said contacting indicates that said test compound is a compound that modulates ligand binding.

* * * * *